(12) United States Patent
Park et al.

(10) Patent No.: US 11,518,849 B2
(45) Date of Patent: Dec. 6, 2022

(54) POST POLYMERIZATION MODIFICATION IN FLOW

(71) Applicants: International Business Machines Corporation, Armonk, NY (US); Agency for Science, Technology and Research, Singapore (SG)

(72) Inventors: Nathaniel H. Park, San Jose, CA (US); Victoria A Piunova, Los Gatos, CA (US); Dmitry Zubarev, San Jose, CA (US); James L. Hedrick, Pleasanton, CA (US); Yi Yan Yang, Singapore (SG); Eddy Wei Ping Tan, Singapore (SG)

(73) Assignees: INTERNATIONAL BUSINESS MACHINES CORPORATION, Armonk, NY (US); AGENCY FOR SCIENCE, TECHNOLOGY AND RESEARCH, Singapore (SG)

( * ) Notice: Subject to any disclaimer, the term of this patent is extended or adjusted under 35 U.S.C. 154(b) by 15 days.

(21) Appl. No.: 16/882,028

(22) Filed: May 22, 2020

(65) Prior Publication Data
US 2021/0363296 A1    Nov. 25, 2021

(51) Int. Cl.
C08G 64/10 (2006.01)
C08G 64/16 (2006.01)
B01J 19/24 (2006.01)
C08G 64/30 (2006.01)
C07D 319/06 (2006.01)

(52) U.S. Cl.
CPC ............. C08G 64/10 (2013.01); B01J 19/24 (2013.01); C07D 319/06 (2013.01); C08G 64/1633 (2013.01); C08G 64/30 (2013.01); B01J 2219/00029 (2013.01)

(58) Field of Classification Search
CPC .................................................. C08G 64/10
USPC ....................................................... 549/228
See application file for complete search history.

(56) References Cited

U.S. PATENT DOCUMENTS

| | | | |
|---|---|---|---|
| 4,603,154 A | 7/1986 | Luetzelschwab | |
| 5,026,791 A | 6/1991 | Hawkins et al. | |
| 5,578,682 A | 11/1996 | White | |
| 8,063,174 B2 | 11/2011 | Klaehn et al. | |
| 8,207,351 B2 * | 6/2012 | Fujiwara | C08G 64/30 528/370 |
| 8,779,166 B2 * | 7/2014 | Hedrick | C08G 64/0233 549/228 |
| 9,556,353 B2 | 1/2017 | Cheng et al. | |
| 9,944,791 B2 | 4/2018 | Davies | |
| 10,023,479 B2 | 7/2018 | Cho et al. | |
| 2017/0210994 A1 * | 7/2017 | Lim | C09K 19/3441 |
| 2019/0177466 A1 | 6/2019 | Hedrick et al. | |
| 2020/0010610 A1 | 1/2020 | Park et al. | |
| 2020/0010612 A1 | 1/2020 | Park et al. | |
| 2020/0010613 A1 | 1/2020 | Park et al. | |

FOREIGN PATENT DOCUMENTS

DE    3627247    *    8/1986    ........... C07D 305/06

OTHER PUBLICATIONS

Rintjema Chemistry—A European Journal (2015), 21(30), 10754-10762.*
Noy, et al., "Para-Fluoro Postpolymerization Chemistry of Poly(pentafluorobenzyl methacrylate): Modification with Amines, Thiols, and Carbonylthiolates," Macromolecules 2017, 50, 7028, 13 pages.
Ott, et al., "Post-modification of poly(pentafluorostyrene): a versatile "click" method to create well-defined multifunctional graft copolymers," U. S. Chem. Commun. 2008, 0, 3516, 3 pages.
Chen, et al., "Tuning H-bond Capability of Hydroxylated-Poly(2,3,4,5,6-pentafluorostyrene) Grafted Copolymers Prepared by Chemoselective and Versatile Thiol-para-fluoro "Click-type" Coupling with Mercaptoalcohols," J. Polym. Sci. A Polym. Chem. 2012, 50, 3452, 9 pages.
Becer, et al., "Clicking Pentafluorostyrene Copolymers: Synthesis, Nanoprecipitation, and Glycosylation," Macromolecules 2009, 42, 2387, 8 pages.
Park et al. "Synthesis of Cyclic Carbonate Monomers" U.S. Appl. No. 16/871,733, filed May 11, 2020, 39 pages.

* cited by examiner

*Primary Examiner* — Nizal S Chandrakumar
(74) *Attorney, Agent, or Firm* — Amin, Turocy & Watson, LLP

(57) ABSTRACT

Techniques regarding post polymerization modifications to polycarbonate polymers via a flow reactor are provided. For example, one or more embodiments described herein can comprise a cyclic carbonate monomer that can be employed to facilitate polymerization of one or more polycarbonate platforms susceptible to post polymerization modification. For instance, one or more embodiments can regard a cyclic carbonate molecular backbone covalently bonded to an aryl halide functional group via in accordance with a chemical structure selected from the group consisting of:

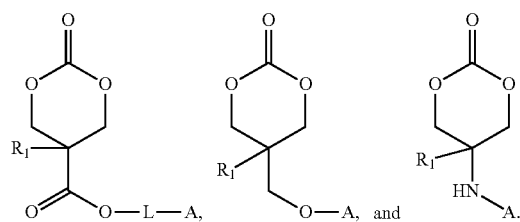

In the chemical structures, "$R_1$" can be selected from the group consisting of a hydrogen atom and a functional group comprising a first alkyl group; "L" can represent a linkage group, comprising: a second alkyl group and an end group having at least one member selected from the group consisting of an oxygen atom and a nitrogen atom; and "A" can represent the aryl halide functional group.

20 Claims, 21 Drawing Sheets

REACTING, VIA A FLOW REACTOR, A LINKAGE CHEMICAL COMPOUND WITH AN ARYL HALIDE COMPOUND TO FORM A FIRST INTERMEDIATE COMPOUND, WHEREIN THE LINKAGE CHEMICAL COMPOUND COMPRISES BETWEEN 1 AND 20 CARBON ATOMS AND AT LEAST ONE END GROUP SELECTED FROM THE GROUP CONSISTING OF A HALIDE, A HYDROXYL GROUP, AND AN AMINO GROUP. — 202

↓

FORMING A SECOND INTERMEDIATE CHEMICAL COMPOUND BY REACTING, VIA THE FLOW REACTOR, THE FIRST INTERMEDIATE COMPOUND WITH A CHEMICAL COMPOUND CHARACTERIZED BY A STRUCTURE SELECTED FROM THE GROUP CONSISTING OF: — 204

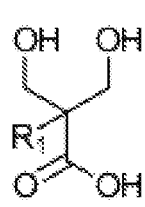 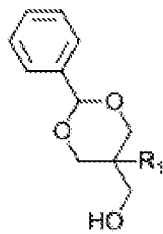 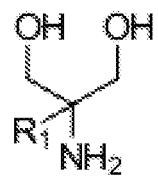

WHEREIN R1 CAN REPRESENT A HYDROGEN ATOM OR AN ALKYL GROUP COMPRISING GREATER THAN OR EQUAL TO 1 CARBON ATOM AND LESS THAN OR EQUAL TO 3 CARBON ATOMS

↓

REACTING, VIA THE FLOW REACTOR, THE SECOND INTERMEDIATE COMPOUND WITH A CARBONYL EQUIVALENT TO FORM A CYCLIC CARBONATE MONOMER FUNCTIONALIZED WITH AN ARYL HALIDE GROUP — 206

FORMING AN INTERMEDIATE CHEMICAL COMPOUND BY REACTING, VIA THE FLOW REACTOR, AN ARYL HALIDE COMPOUND WITH A CHEMICAL COMPOUND CHARACTERIZED BY ONE OF THE FOLLOWING STRUCTURES: — 302

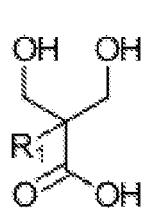 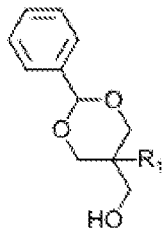 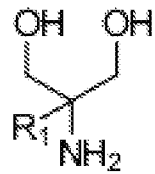

WHEREIN R1 CAN REPRESENT A HYDROGEN ATOM AN ALKYL GROUP COMPRISING GREATER THAN OR EQUAL TO 1 CARBON ATOM AND LESS THAN OR EQUAL TO 3 CARBON ATOMS

REACTING, VIA THE FLOW REACTOR, THE INTERMEDIATE COMPOUND WITH ONE OR MORE CARBONYL EQUIVALENTS TO FORM A CYCLIC CARBONATE MONOMER FUNCTIONALIZED WITH AN ARYL HALIDE GROUP — 304

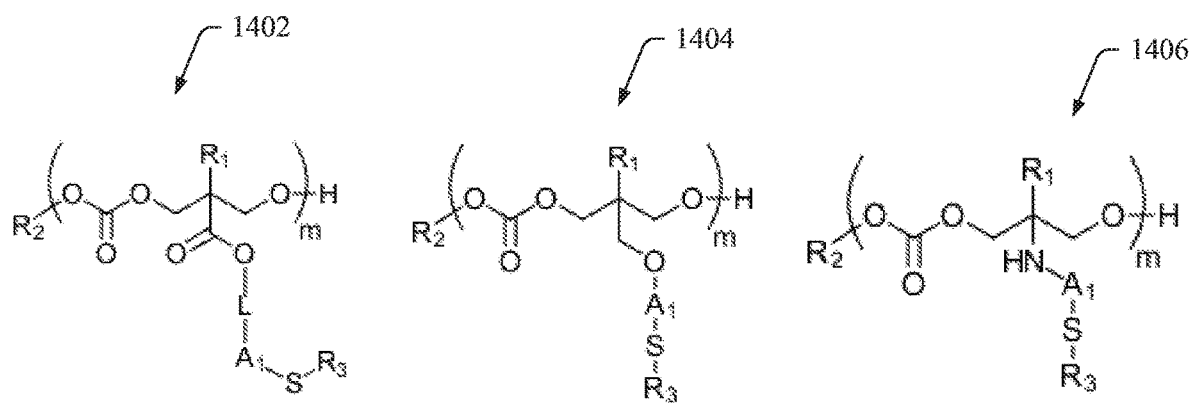
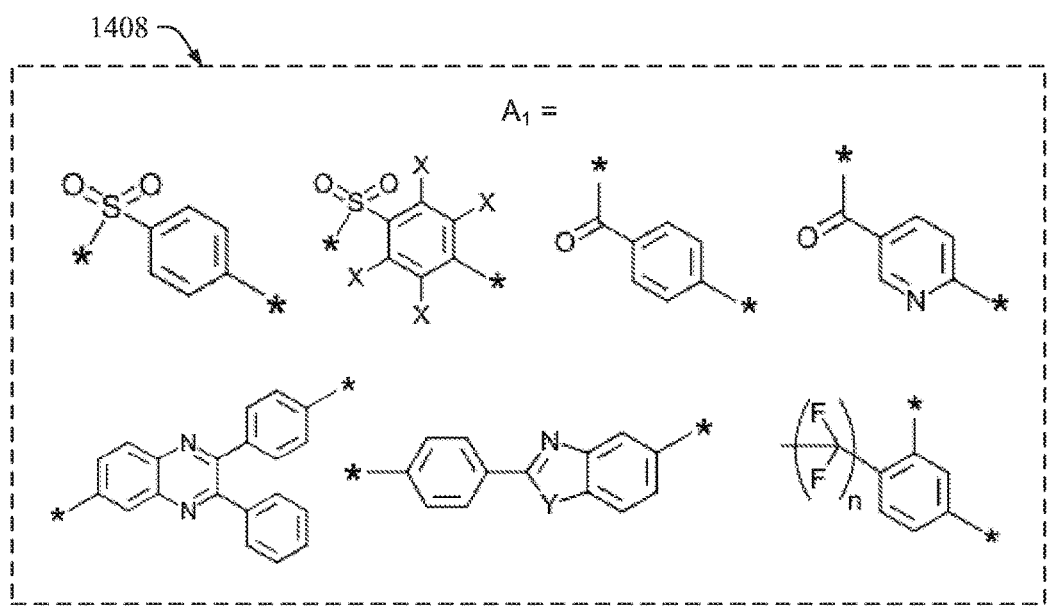
FIG. 14

```
┌─────────────────────────────────────────────────────┐
│ PERFORMING, VIA A FLOW REACTOR, A ROP OF A CYCLIC   │
│ CARBONATE MONOMER TO FORM A POLYCARBONATE           │── 1502
│ POLYMER, WHEREIN THE CYCLIC CARBONATE MONOMER       │
│ COMPRISES AN ARYL HALIDE GROUP                      │
└─────────────────────────────────────────────────────┘
                          │
                          ▼
┌─────────────────────────────────────────────────────┐
│ REACTING THE POLYCARBONATE POLYMER WITH A           │
│ TRIMETHYLSILYL PROTECTED THIOL COMPOUND, WHEREIN    │── 1504
│ THE TRIMETHYLSILYL PROTECTED THIOL COMPOUND         │
│ COMPRISES A TARGET FUNCTIONAL GROUP THAT            │
│ COVALENTLY BONDS TO THE ARYL HALIDE GROUP           │
└─────────────────────────────────────────────────────┘
```

POST POLYMERIZATION MODIFICATION IN FLOW

BACKGROUND

The subject disclosure relates to one or more methods of post polymerization modifications to polycarbonate polymers via a flow reactor, and more specifically, to the synthesis of cyclic carbonate monomers comprising one or more functional groups that can enable modifications post a ring-opening polymerization ("ROP") within a flow reactor.

SUMMARY

The following presents a summary to provide a basic understanding of one or more embodiments of the invention. This summary is not intended to identify key or critical elements, or delineate any scope of the particular embodiments or any scope of the claims. Its sole purpose is to present concepts in a simplified form as a prelude to the more detailed description that is presented later. In one or more embodiments described herein, chemical compounds, synthesis methods, and modification methods that can regard post polymerization modification of polycarbonate polymers are described.

According to an embodiment, a monomer is provided. The monomer can comprise a cyclic carbonate molecular backbone covalently bonded to an aryl halide functional group via in accordance with a chemical structure selected from the group consisting of:

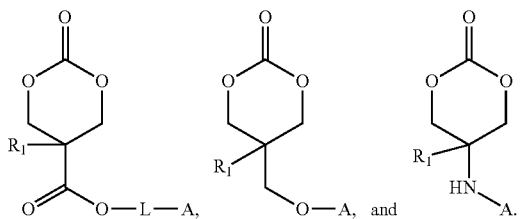

In the chemical structures, "$R_1$" can be selected from the group consisting of a hydrogen atom and a first alkyl group; "L" can represent a linkage group, comprising: a second alkyl group and an end group having at least one member selected from the group consisting of an oxygen atom and a nitrogen atom; and "A" can represent the aryl halide functional group.

According to an embodiment, a polymer is provided. The polymer can comprise a polycarbonate molecular backbone covalently bonded to a target functional group via an pendent functional group in accordance with a chemical structure selected from the group consisting of:

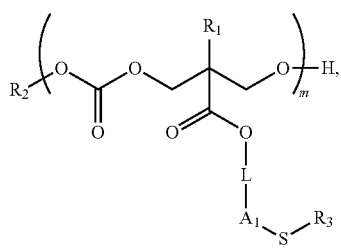

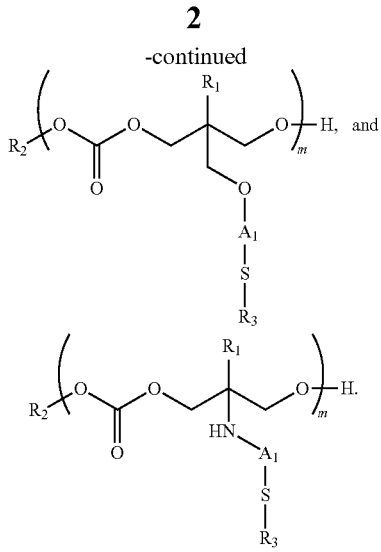

In the chemical structures, "$R_1$" can be selected from the group consisting of a hydrogen atom and a first alkyl group; "$R_2$" can represent a functional group derived from a compound comprising an alcohol group; "L" can represent a linkage group, comprising: a second alkyl group and an end group having at least one member selected from the group consisting of an oxygen atom and a nitrogen atom; "$A_1$" can represent the pendent functional group and comprise an aryl group; "$R_3$" can represent the target functional group; and "m" can represent an integer greater than or equal to 2 and less than or equal to 1,000.

According to an embodiment, a method is provided. The method can comprise performing, via a flow reactor, a ring-opening polymerization of a cyclic carbonate monomer to form a polycarbonate polymer characterized by a chemical structure selected from the group consisting of:

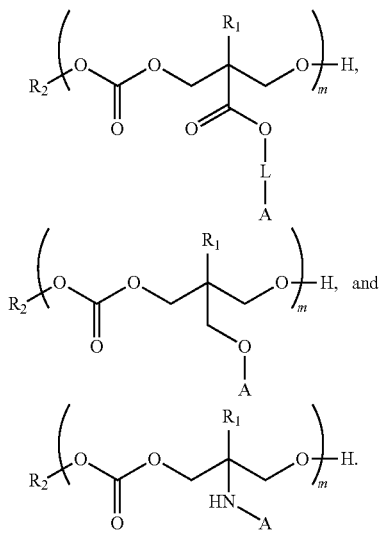

In the chemical structures, "$R_1$" can be selected from the group consisting of a hydrogen atom and a first alkyl group; "$R_2$" can represent a functional group derived from a compound comprising an alcohol group; "L" can represent a linkage group, comprising: a second alkyl group and an end group having at least one member selected from the group consisting of an oxygen atom and a nitrogen atom;

"A" can represent an aryl halide group; and "m" can represent an integer greater than or equal to two and less than or equal to 1,000.

BRIEF DESCRIPTION OF THE DRAWINGS

FIG. 2 illustrates a flow diagram of an example, non-limiting method that can facilitate synthesizing one or more cyclic carbonate monomers that can be utilized to polymerization polycarbonate polymers that are susceptible to post polymerization modification accordance with one or more embodiments described herein.

FIG. 3 illustrates a flow diagram of an example, non-limiting method that can facilitate synthesizing one or more cyclic carbonate monomers that can be utilized to polymerization polycarbonate polymers that are susceptible to post polymerization modification accordance with one or more embodiments described herein.

FIG. 14 illustrates a diagram of example, non-limiting chemical structures that can characterize one or more polycarbonate polymers that can be achieved via one or more post polymerization nucleophilic aromatic substitution reactions in accordance with one or more embodiments described herein.

FIG. 15 illustrates a flow diagram of an example, non-limiting method that can facilitate polymerization and/or post polymerization modification of one or more functionalized polycarbonate polymers in accordance with one or more embodiments described herein.

DETAILED DESCRIPTION

The following detailed description is merely illustrative and is not intended to limit embodiments and/or application or uses of embodiments. Furthermore, there is no intention to be bound by any expressed or implied information presented in the preceding Background or Summary sections, or in the Detailed Description section.

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details.

Numerous chemical process industries retain batch processing as their primary method of manufacture. For example, products traditionally manufactured by batch processing can include polycarbonate platforms that serve as the foundation for many modern-day applications such as therapeutic delivery and macromolecular therapeutics. However, batch processing can be time-consuming, require the design of manufacturing stages that can be difficult to reproduce, can necessitate adverse safety conditions (e.g., due to the transportation of chemicals and/or storage of volatile chemicals), can require a large labor force, and/or can be difficult to automate.

Various embodiments described herein can regard forming one or more functionalized cyclic carbonate monomers that can synthesize one or more polycarbonate polymers via one or more ROPs. Further, the cyclic carbonate monomers can be functionalized with one or more aryl halide compounds that can facilitate post polymerization modification of the one or more polycarbonate polymers. One or more embodiments can leverage the uniquely enabling aspects of continuous-flow synthesis and a class of highly active ring-opening polymerization catalysts to rapidly access the polycarbonate platforms. In addition, one or more embodiments can employ trimethylsilyl functional thiols as nucleophiles in a post polymerization scheme that can enable polymer modification of the polycarbonates without significantly altering the flowrate of the continuous-flow synthesis.

As used herein, the term "flow reactor" can refer to a device in which one or more chemical reactions can take place within one or more channels (e.g., microfluidic channels). For example, a flow reactor can facilitate continuous flow production, as opposed to batch production. One or more streams of chemical reactants can flow (e.g., continuously) through the one or more channels of the flow reactor, wherein one or more chemical reactions (e.g., polymerizations, protonations, and/or deprotonations) involving the chemical reactants can occur within the one or more channels as the one or more streams flow.

Figure 1:
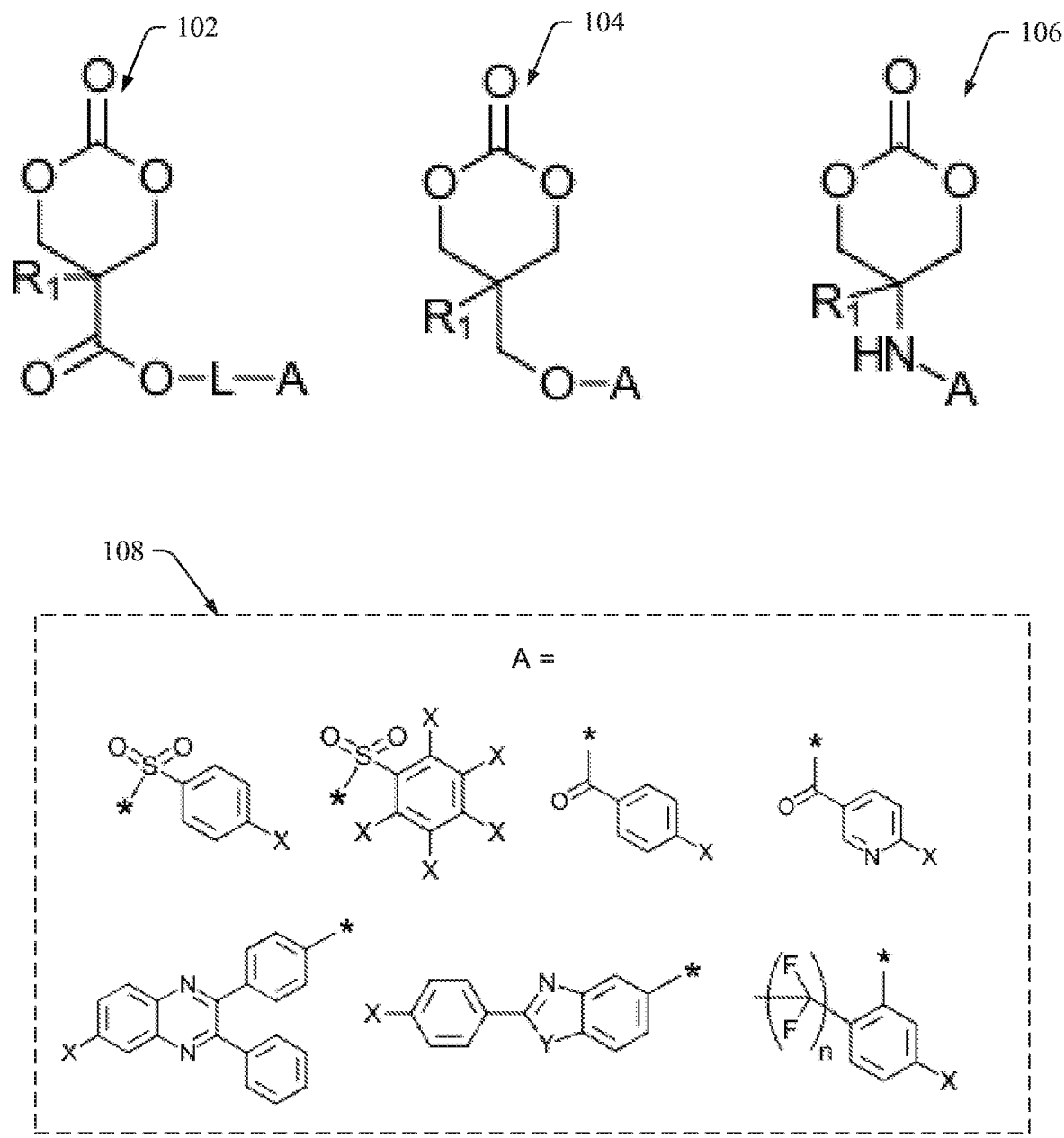
FIG. 1 illustrates a diagram of example, non-limiting chemical structures that can characterize one or more cyclic carbonate monomers that can be utilized to polymerization polycarbonate polymers that are susceptible to post polymerization modification accordance with one or more embodiments described herein.

FIG. 1 illustrates a diagram of example, non-limiting first cyclic carbonate chemical structure 102, second cyclic carbonate chemical structure 104, and third cyclic carbonate chemical structure 106 that can characterize one or more functionalized cyclic carbonate monomers in accordance with one or more embodiments described herein. Repetitive description of like elements employed in other embodiments described herein is omitted for sake of brevity. "$R_1$" can represent a first functional group comprising a hydrogen atom or an alkyl group having greater than or equal to one carbon atom and less than or equal to 3 carbon atoms. Example alkyl groups that can be represented by "$R_1$" can include, but are not limited: a methyl group, an ethyl group, a propyl group, etc., and/or the like.

Also shown in FIG. 1, the first cyclic carbonate chemical structure 102 can comprise one or more aryl halide groups (e.g., represented by "A") can be covalently bonded to a first carbonate molecular backbone via one or more linkage groups (e.g., represented by "L"). In various embodiments, the one or more linkage groups (e.g., represented by "L") can comprise: an alkyl chain having greater than or equal to one carbon atom and less than or equal to 20 carbon atoms; and/or aryl rings. Further, the one or linkage groups (e.g., represented by "L") can comprise one or more end groups that include, for example, heteroatoms such as an oxygen or nitrogen atom bonded to the one or more aryl halide groups (e.g., represented by "A") and/or carbonate molecular backbone. Additionally, the second cyclic carbonate chemical structure 104 can comprise the one or more aryl halide groups (e.g., represented by "A") directly bonded to an oxygen atom of a second carbonate molecular backbone. Moreover, the third cyclic carbonate chemical structure 106 can comprise the one or more aryl halide groups (e.g., represented by "A") directly bonded to a nitrogen atom of a third carbonate molecular backbone.

One or more example aryl halide structures 108 are also shown in FIG. 1, wherein the "*" can delineate a connection to the one or more linkage groups (e.g., represented by "L") or respective carbonate molecular backbones. Further, "X" can represent a halide (e.g., a fluorine atom, a chloride atom, a bromine atom, or an iodine atom). In one or more embodiments, "X" can represent a fluorine atom. Further, "Y" can represent an oxygen atom, —NH—, or a sulfur atom. Additionally, "n" can represent an integer greater than or equal to 1 and less than or equal to 8. One of ordinary skill in the art will recognize that the position of the one or more halides on the aryl ring can vary.

In various embodiments described herein, the aryl halide group (e.g., represented by "A") can facilitate a post polymerization modification to one or more polycarbonate platforms formed from the functionalized cyclic carbonate monomers characterized the first cyclic carbonate chemical structure 102, the second cyclic carbonate chemical structure 104, and/or the third cyclic carbonate chemical structure 106. For example, the one or more aryl halide groups can activate one or more nucleophilic aromatic substitutions to facilitate a post polymerization modification. For instance, the one or more aryl halide groups (e.g., represented by "A"), and their delineated position within the first cyclic carbonate chemical structure 102, second cyclic carbonate chemical structure 104, and/or third cyclic carbonate chemical structure 106, can facilitate one or more: ketone-activated nucleophilic aromatic substitutions, imidazole-activated nucleophilic aromatic substitutions, quinoxaline-activated nucleophilic aromatic substitutions, ester-activated nucleophilic aromatic substitutions, amide-activated nucleophilic aromatic substitutions, and/or sulfonyl-activated nucleophilic aromatic substitutions. In various embodiments, one or more of the halides (e.g., represented by "X") of the aryl halide groups (e.g., represented by "A") can be activated towards displacement by the one or more nucleophilic aromatic substitutions during the post polymerization modifications described herein.

FIG. 2 illustrates a flow diagram of an example, non-limiting method 200 that can facilitate forming the one or more functionalized cyclic carbonate monomers characterized the first cyclic carbonate chemical structure 102 in accordance with one or more embodiments described herein. Repetitive description of like elements employed in other embodiments described herein is omitted for sake of brevity.

At 202, the method 200 can comprise reacting, via a flow reactor, one or more linkage chemical compounds with one or more aryl halide compounds to form a first intermediate compound, wherein the one or more linkage chemical compounds can comprise greater than or equal to 1 carbon atom and less than or equal to 20 carbon atoms. Further, the one or more linkage chemical compounds can comprise at least one end group selected from the group consisting of: a halide, a hydroxyl group, an amino group, a combination thereof, and/or the like. In one or more embodiments, the one or more linkage chemical compounds can comprise one or more aryl rings.

At 204, the method 200 can comprise forming a second intermediate chemical compound by reacting, via the flow reactor, the first intermediate compound with a molecular backbone characterized by the following structure:

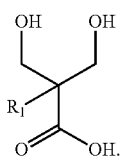

"R$_1$" can represent a hydrogen atom or a first functional group comprising an alkyl group having greater than or equal to one carbon atom and less than or equal to 3 carbon atoms. For example, the first intermediate compound can be reacted with dimethylolpropionic acid ("DMPA") at 202.

At 206, the method 200 can comprise reacting, via the flow reactor, the second intermediate compound with one or more carbonyl equivalents to form a cyclic carbonate monomer functionalized with an aryl halide group. Example carbonyl equivalents can include, but are not limited to: triphosgene, bis-pentafluorophenyl carbonate, N,N-carbonyldiimidazole, methyl chloroformate, ethyl chloroformate, diphenyl carbonate, diethyl carbonate, dimethyl carbonate, N,N'-Disuccinimidyl carbonate, a combination thereof, and/or the like. For example, the cyclic carbonate monomer formed at 206 can be characterized by the first cyclic carbonate chemical structure 102. For instance, the molecular backbone of the cyclic carbonate monomer can be derived from the chemical compound at 204. Also, the one or more linkage groups (e.g., represented by "L") can be derived from the one or more linkage chemical compounds at 202, and the aryl halide group (e.g., represented by "A") can be derived from the one or more alky halide compounds at 202.

FIG. 3 illustrates a flow diagram of an example, non-limiting method 300 that can facilitate forming the one or more functionalized cyclic carbonate monomers characterized the first cyclic carbonate chemical structure 102, the second cyclic carbonate chemical structure 104, and/or the third cyclic carbonate chemical structure 106 in accordance with one or more embodiments described herein. Repetitive description of like elements employed in other embodiments described herein is omitted for sake of brevity.

At 302, the method 300 can comprise forming an intermediate chemical compound by reacting, via the flow reactor, an aryl halide compound with a molecular backbone characterized by one of the following structures:

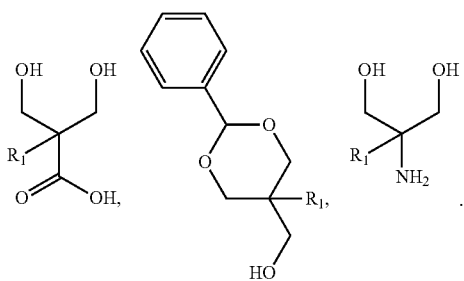

"R$_1$" can represent a hydrogen atom or a first functional group comprising an alkyl group having greater than or equal to one carbon atom and less than or equal to 3 carbon atoms. For example, the first intermediate compound can be reacted with DMPA at 302.

At 304, the method 300 can comprise reacting, via the flow reactor, the intermediate compound with one or more carbonyl equivalents to form a cyclic carbonate monomer functionalized with an aryl halide group. Example carbonyl equivalents can include, but are not limited to: triphosgene, bis-pentafluorophenyl carbonate, N,N-carbonyldiimidazole, methyl chloroformate, ethyl chloroformate, diphenyl carbonate, diethyl carbonate, dimethyl carbonate, N,N'-Disuccinimidyl carbonate, a combination thereof, and/or the like. For example, the cyclic carbonate monomer formed at 304 can be characterized by the first cyclic carbonate chemical structure 102, the second cyclic carbonate chemical structure 104, and/or the third cyclic carbonate chemical structure 106. With regards to cyclic carbonate monomers formed at 304 and characterized by first cyclic carbonate chemical structure 102, the one or more linkage groups (e.g., represented by "L") can be derived from the one or more alky halide compounds at 302.

Figure 4A:
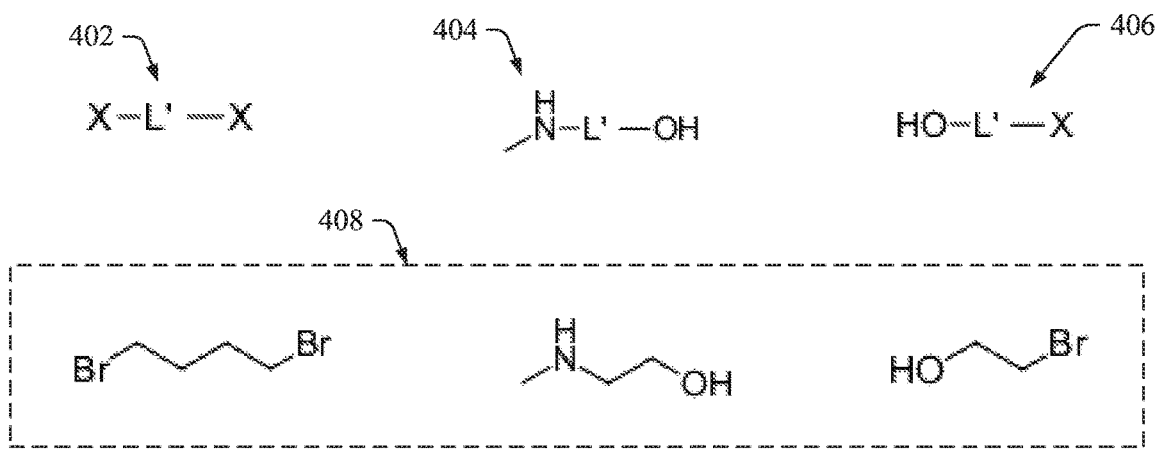
FIG. 4A illustrates a diagram of example, non-limiting chemical structures that can characterize one or more linkage chemical compounds that can be utilized in the synthesis of one or more functionalized cyclic carbonate monomers in accordance with one or more embodiments described herein.

FIG. 4A illustrates a diagram of example, non-limiting chemical structures that can characterize one or more linkage chemical compounds that can be employed to synthesis the one or more functionalized cyclic carbonate monomers characterized by the first cyclic carbonate chemical structure 102 in accordance with one or more embodiments described herein. Repetitive description of like elements employed in other embodiments described herein is omitted for sake of brevity.

As shown in FIG. 4A, chemical structure 402 can characterize a first type of linkage chemical compound comprising the one or more alkyl groups and/or aryl rings (e.g., represented by "L'"), and two halide end groups (e.g., wherein the halides are presented by "X"). For example, the halide end groups (e.g., represented by "X") can be positioned at opposite ends of the one or more alkyl groups and/or aryl rings (e.g., represented by "L'"). Chemical structure 404 can characterize a second type of linkage chemical compound comprising one or more alkyl groups and/or aryl rings (e.g., represented by "L'"), a first end group comprising an amino group, and a second end group comprising a hydroxyl group. For example, the amino group and the hydroxyl group can be positioned at opposite ends of the one or more alkyl groups and/or aryl rings (e.g., represented by "L'"). Chemical structure 406 can characterize a third type of linkage chemical compound comprising one or more alkyl groups and/or aryl rings (e.g., represented by "L'"), a first end group comprising a hydroxyl group, and a second end group comprising a halide (e.g., represented by "X"). Further, example linkage chemical compounds 408 of each chemical structure 402, 404, and 406 are shown in FIG. 4A.

In various embodiments, the one or more linkage groups (e.g., represented by "L") can be derived from the one or more linkage chemical compounds characterized by chemical structure 402, 404, or 406. For example, the one or more alkyl groups and/or aryl rings of the one or more linkage chemical compounds (e.g., represented by "L'") can be the one or more alkyl groups and/or aryl rings comprised within the one or more linkage groups (e.g., represented by "L"). Further, a first of the end groups of the linkage chemical compound (e.g., a halide, a hydroxyl group, or an amino group) can facilitate a bond with the one or more aryl halide groups. Additionally, a second of the end groups of the linkage chemical compound (e.g., a halide, a hydroxyl group, or an amino group) can facilitate a bond with the carbonate molecular backbone.

Figure 4B:
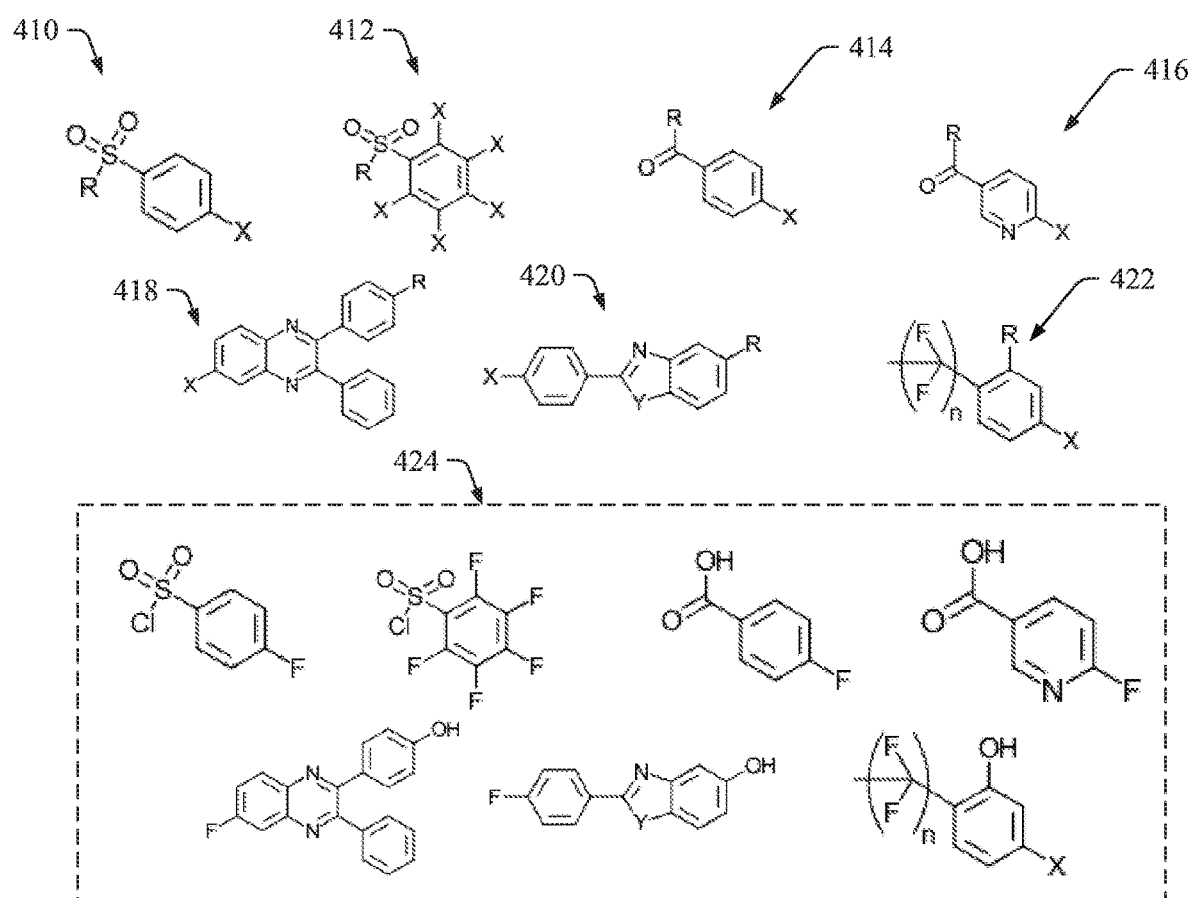
FIG. 4B illustrates a diagram of example, non-limiting chemical structures that can characterize one or more aryl halide compounds that can be utilized in the synthesis of one or more functionalized cyclic carbonate monomers in accordance with one or more embodiments described herein.

FIG. 4B illustrates a diagram of example, non-limiting chemical structures that can characterize one or more aryl halide compounds that can be employed to synthesis the one or more functionalized cyclic carbonate monomers characterized by the first cyclic carbonate chemical structure 102, the second cyclic carbonate chemical structure 104, and/or the third cyclic carbonate chemical structure 106 in accordance with one or more embodiments described herein. Repetitive description of like elements employed in other embodiments described herein is omitted for sake of brevity.

As shown in FIG. 4B, chemical structure 410 can characterize a first type of aryl halide compound, chemical structure 412 can characterize a second type of aryl halide compound, chemical structure 414 can characterize a third type of aryl halide compound, chemical structure 416 can characterize a fourth type of aryl halide compound, chemical structure 418 can characterize a fifth type of aryl halide compound, chemical structure 420 can characterize a fifth type of aryl halide compound, and/or chemical structure 422 can characterize a sixth type of aryl halide compound. Moreover, example aryl halide compounds 424 of each chemical structure 410, 412, 414, 416, 418, 420, and 422 are shown in FIG. 4B.

In various embodiments, "R" can represent a functional group that can facilitate a covalent bonding between the one or more aryl halide groups (e.g., delineated as "A" in FIG. 1) of the aryl halide compounds and the one or more linkage groups (e.g., represented by "L" in FIG. 1) derived from the one or more linkage chemical compounds exemplified in FIG. 4A. In one or more embodiments, the functional group (e.g., represented by "R") can facilitate a covalent bonding between the one or more aryl halide groups (e.g., delineated by "A" in FIG. 1) of the aryl halide compounds and the respective carbonate molecular backbone. Example functional groups that can be "R" can include, but are not limited to: a halide, a hydroxyl group, a carboxyl group, an acyl chloride group, and alkyl group, a combination thereof (e.g., $CH_2Br$, $CH_2Cl$), and/or the like. As described herein, "X" can represent a halide atom. In various embodiments, during synthesis of the one or more functionalized cyclic carbonate monomers characterized by the first cyclic carbonate chemical structure 102, the aryl halide group's bond to functional group "R" can be replaced with a bond to the alkyl group and/or aryl ring of the one or more linkage chemical compounds (e.g., a direct bond, or a bond facilitated by a hydroxyl or amino end group of the linkage chemical compound). Further, an opposite end of the linkage chemical compound's alkyl group can be bonded to the carbonate molecular backbone (e.g., a direct bond, or a bond facilitated by a hydroxyl or amino end group of the linkage chemical compound); thereby linking the aryl halide group to the carbonate molecular backbone. In various embodiments, during synthesis of the one or more functionalized cyclic carbonate monomers characterized by the first cyclic carbonate chemical structure 102, the second cyclic carbonate chemical structure 104, and/or the third cyclic carbonate chemical structure 106, the aryl halide group's bond to functional group "R" can be replaced with a bond to the respective carbonate molecular backbone.

Figure 5:
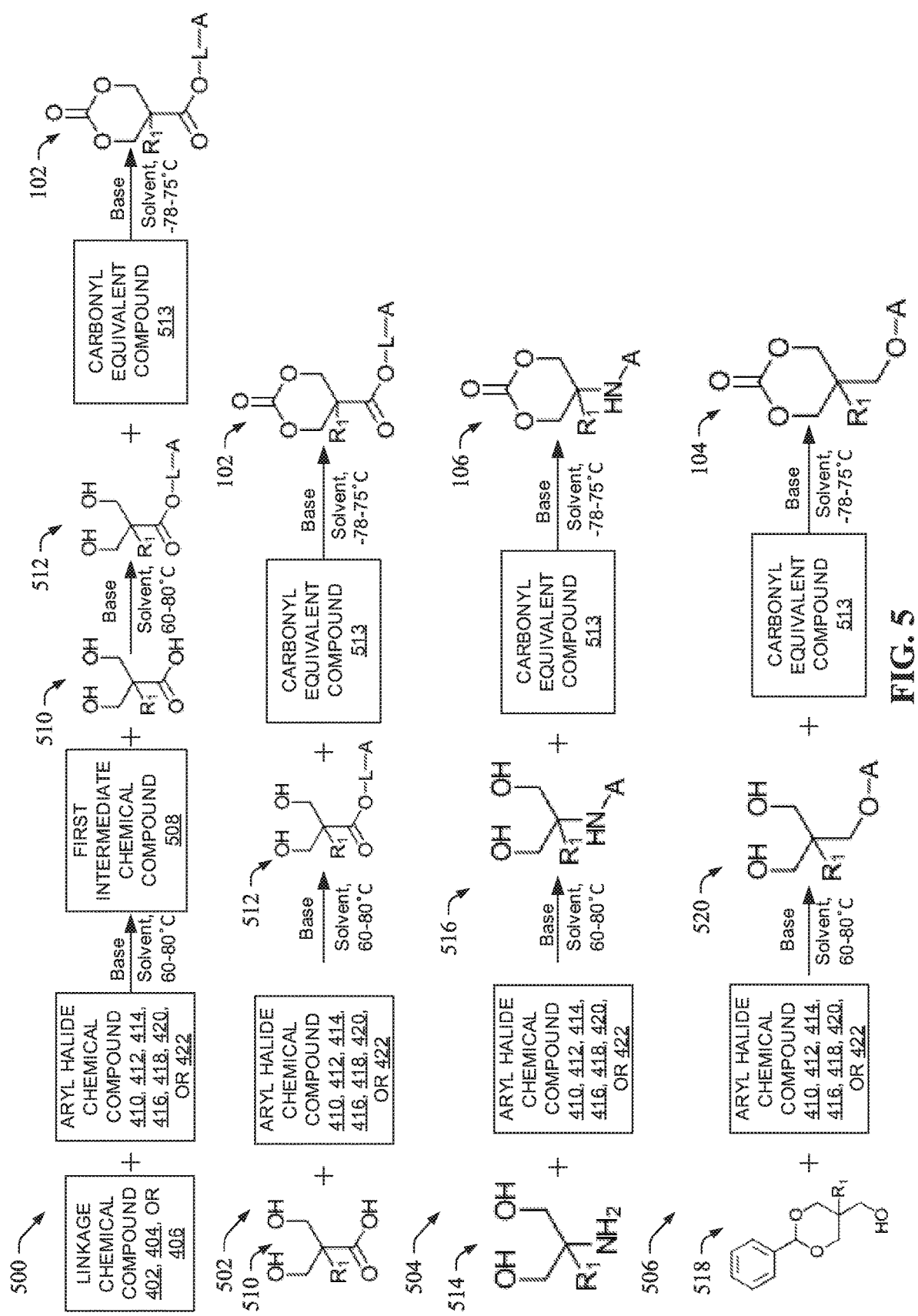
FIG. 5 illustrates a diagram of example, non-limiting synthesis schemes that can characterize the synthesis of one or more functionalized cyclic carbonate monomers in accordance with one or more embodiments described herein.

FIG. 5 illustrates a diagram of example, non-limiting synthesis schemes that can be employed to form one or more functionalized cyclic carbonate monomers characterized by the first cyclic carbonate chemical structure 102, the second cyclic carbonate chemical structure 104, and/or the third cyclic carbonate chemical structure 106 in accordance with one or more embodiments described herein. Repetitive description of like elements employed in other embodiments described herein is omitted for sake of brevity. For example, synthesis schemes 500 and 502 can be employed to form one or more functionalized cyclic carbonate monomers characterized by the first cyclic carbonate chemical structure 102. Synthesis scheme 504 can be employed to form one or more functionalized cyclic carbonate monomers characterized by the second cyclic carbonate chemical structure 104. Synthesis scheme 506 can be employed to form one or more functionalized cyclic carbonate monomers characterized by the third cyclic carbonate chemical structure 106. In various embodiments, synthesis scheme 500 can include the various features of method 200, and synthesis schemes 502, 504, and/or 506 can include the various features of method 300.

At a first stage of synthesis scheme 500, one or more linkage chemical compounds can be reacted with one or more aryl halide chemical compounds to form a first intermediate chemical compound 508. For example, the one or more linkage chemical compounds can be characterized by chemical structure 402, 404, or 406. Also, the one or more aryl halide chemical compounds can be characterized by chemical structure 410, 412, 414, 416, 418, 420, or 422. In various embodiments, the one or more linkage chemical compounds and/or aryl halide chemical compounds can be reacted via one or more alkylation reaction conditions and/or coupling reaction conditions. As used herein, the term "alkylation reaction conditions" can refer to chemical reaction conditions in which the described reactants are reacted in the presence of a base (e.g., 1.2-1.8 equivalents of base), a solvent, and a temperature greater than or equal to 60 degrees Celsius (° C.) and less than or equal to 80° C. Example bases that can be employed in the alkylation procedure can include, but are not limited to: triethylamine ("$Et_3N$"), diisopropylethylamine, potassium carbonate, potassium phosphate, sodium hydroxide, potassium hydroxide, a combination thereof, and/or the like. Example solvents that can be employed in the alkylation procedure can include, but are not limited to: dimethylformamide ("DMF"), dimethylacetamide ("DMA"), acetonitrile, dimethyl sulfoxide ("DMSO"), tetrahydrofuran ("THF"), THF: Water, a combination thereof, and/or the like. As used herein, the term "coupling reaction conditions" can refer to chemical reaction conditions in which the described reactants are reacted in the presence of a coupling reagent (e.g., 1.1 equivalents), 4-N, N-dimethylaminopyridine (e.g., 1.1 equivalents), a solvent, and a temperature greater than or equal to 0° C. and less than or equal to 22° C. Example coupling reagents that can be employed in the coupling reaction conditions can include, but are not limited to: 1-ethyl-3-(3-dimethylaminopropyl)carbodiimide, diisopropylcarbodiimide, dicyclohexyldicarbodiimide, a combination thereof, and/or the like. Example solvents that can be employed in the coupling reaction conditions can include, but are not limited to: chloroform, dichloromethane, THF, acetonitrile, a combination thereof, and/or the like. For instance, FIG. 5 depicts an embodiment of the first stage of synthesis scheme 500 in which the one or more linkage chemical compounds and aryl halide chemical compounds are react in the presence of one or more alkylation reaction conditions. At a second stage of synthesis scheme 500, the intermediate chemical compound can be reacted with a first molecular backbone monomers characterized by chemical structure 510 to form a second intermediate chemical compound characterized by chemical structure 512. In various embodiments, the second stage of synthesis scheme 500 can be facilitated by the one or more alkylation reaction condition or coupling reaction conditions. For instance, FIG. 5 depicts an embodiment of the second stage of synthesis scheme 500 in which the one or more first intermediate chemical compounds 508 and first molecular backbone monomers characterized by chemical structure 510 are reacted in the presence of one or more alkylation reaction conditions. At a third stage of the synthesis scheme 500, the second intermediate chemical compound can be reacted with one or more carbonyl equivalent compounds 513 to form a functionalized cyclic carbonate monomer that can be characterized by the first cyclic carbonate chemical structure 102. Example carbonyl equivalent compounds 513 can include, but are not limited to: triphosgene, bis-pentafluorophenyl carbonate, N,N-carbonyldiimidazole, methyl chloroformate, ethyl chloroformate, diphenyl carbonate, diethyl carbonate, dimethyl carbonate, N,N'-Disuccinimidyl carbonate, a combination thereof, and/or the like. In various embodiments, the third stage of synthesis scheme 500 can be facilitated by one or more carbonate reaction conditions. As used herein, the term "carbonate reaction conditions" can refer to one or more to chemical reaction conditions in which the described reactants are reacted in the presence of a base (e.g., 1.2 to 4 equivalents of base), a solvent, and a temperature greater than or equal to −78° C. and less than or equal to 75° C. Example bases that can be employed in the one or more carbonate reaction conditions can include, but are not limited to: $Et_3N$, diisopropyl ethylamine, a combination thereof, and/or the like. Example solvents that can be employed in the one or more carbonate reaction conditions can include, but are not limited to: dichloromethane, chloroform, acetonitrile, MeCN, a combination thereof, and/or the like.

At a first stage of synthesis scheme 502, the one or more molecular backbone monomers characterized by chemical structure 510 can be reacted with one or more aryl halide chemical compounds to form a functionalized monomer compound characterized by chemical structure 512. For example, the one or more aryl halide chemical compounds can be characterized by chemical structure 410, 412, 414, 416, 418, 420, or 422. In various embodiments, the first stage of synthesis scheme 502 can be facilitated by alkylation reaction conditions or coupling reaction conditions. For instance, FIG. 5 depicts an embodiment in which the one or more molecular backbone monomers characterized by chemical structure 510 and aryl halide chemical compounds characterized by chemical structure 410, 412, 414, 416, 418, 420, or 422 can be reacted together in the presence of alkylation reaction conditions. At a second stage of the synthesis scheme 502, the intermediate chemical compound can be reacted with one or more carbonyl equivalent compounds to form a functionalized cyclic carbonate monomer that can be characterized by first cyclic carbonate chemical structure 102. In various embodiments, the second stage of synthesis scheme 502 can be facilitated by one or more carbonate reaction conditions.

At a first stage of synthesis scheme 504, one or more molecular backbone monomers characterized by chemical structure 514 can be reacted with one or more aryl halide chemical compounds to form a functionalized monomer compound characterized by chemical structure 516. For example, the one or more aryl halide chemical compounds can be characterized by chemical structure 410, 412, 414, 416, 418, 420, or 422. In various embodiments, the first stage of synthesis scheme 504 can be facilitated by alkylation reaction conditions or coupling reaction conditions. For instance, FIG. 5 depicts an embodiment in which the one or more molecular backbone monomers characterized by chemical structure 514 and aryl halide chemical compounds characterized by chemical structure 410, 412, 414, 416, 418, 420, or 422 can be reacted together in the presence of alkylation reaction conditions. At a second stage of the synthesis scheme 504, the intermediate chemical compound can be reacted with one or more carbonyl equivalent compounds 513 to forma functionalized cyclic carbonate monomer that can be characterized by the third cyclic carbonate chemical structure 106. In various embodiments, the second stage of synthesis scheme 504 can be facilitated by one or more carbonate reaction conditions.

At a first stage of synthesis scheme 506, one or more molecular backbone monomers characterized by chemical structure 518 can be reacted with one or more aryl halide chemical compounds to form an intermediate chemical compound characterized by chemical structure 520. For example, the one or more aryl halide chemical compounds can be characterized by chemical structure 410, 412, 414, 416, 418, 420, or 422. In various embodiments, the first stage of synthesis scheme 506 can be facilitated by alkylation reaction conditions or coupling reaction conditions. For instance, FIG. 5 depicts an embodiment in which the one or more molecular backbone monomers characterized by chemical structure 518 and aryl halide chemical compounds characterized by chemical structure 410, 412, 414, 416, 418, 420, or 422 can be reacted together in the presence of alkylation reaction conditions. At a second stage of the synthesis scheme 506, the intermediate chemical compound can be reacted with one or more carbonyl equivalent compounds 513 to form a functionalized cyclic carbonate monomer that can be characterized by the second cyclic carbonate chemical structure 104. In various embodiments, the second stage of synthesis scheme 506 can be facilitated by one or more carbonate reaction conditions.

Figure 6:
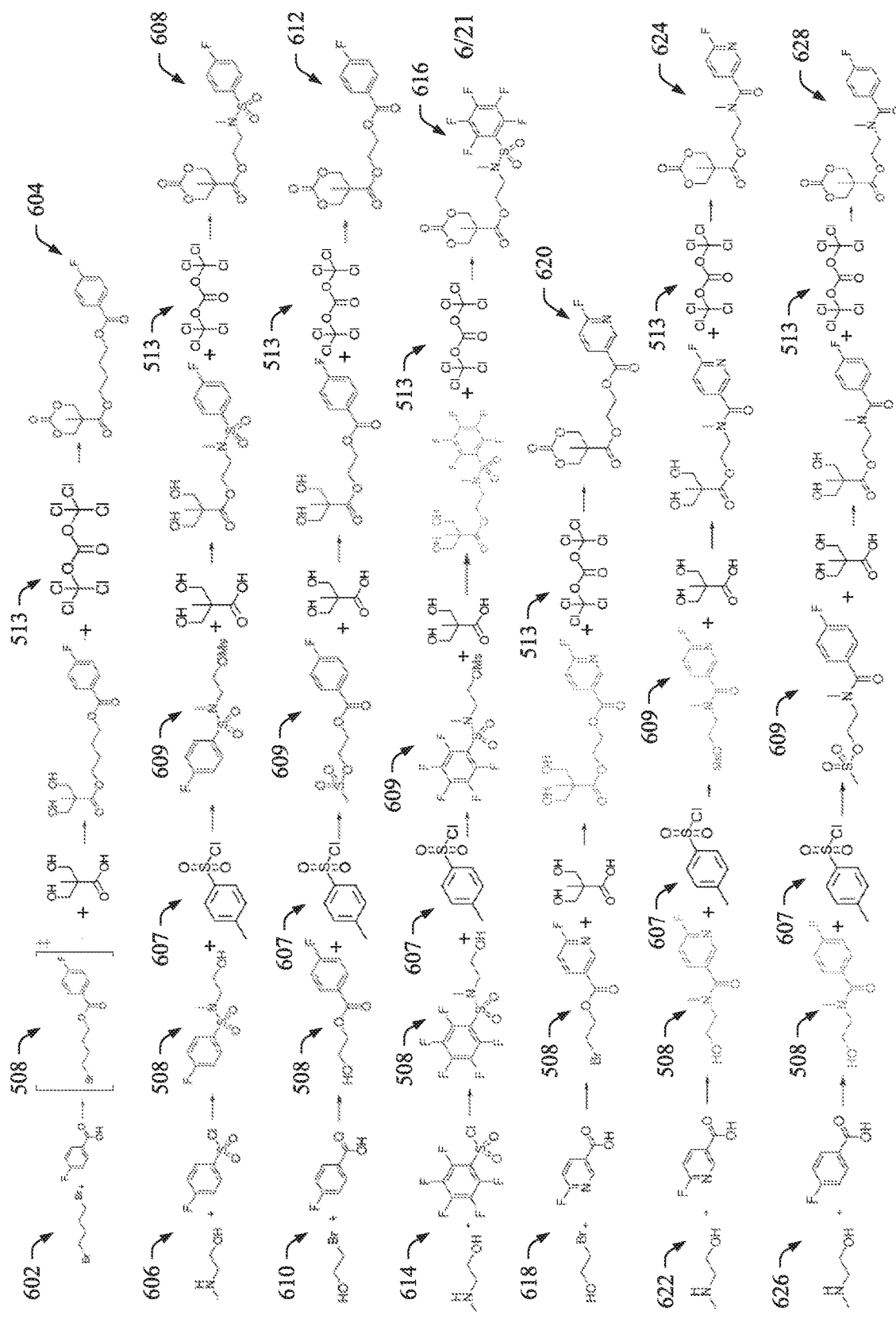
FIG. 6 illustrates a diagram of example, non-limiting synthesis schemes that can exemplify one or more synthesis schemes characterizing the formation of one or more functionalized cyclic carbonate monomers in accordance with one or more embodiments described herein.

FIG. 6 illustrates a diagram of non-limiting example synthesis schemes that can exemplify formation of one or more functionalized cyclic carbonate monomers characterized by the first cyclic carbonate chemical structure 102 in accordance with one or more embodiments described herein. Repetitive description of like elements employed in other embodiments described herein is omitted for sake of brevity. In various embodiments, the one or more exemplary synthesis schemes depicted in FIG. 6 can exemplify the features of synthesis scheme 500 and method 200.

As shown in FIG. 6, synthesis scheme 602 can be employed to form functionalized cyclic carbonate monomer 604. For example, a first stage of synthesis scheme 602 can form a first intermediate chemical compound 508 by reacting a linkage chemical compound characterized by chemical structure 402 with an aryl halide compound characterized by chemical structure 414. In various embodiments, the first stage of synthesis scheme 602 can be facilitated by alkylation reaction conditions or coupling reaction conditions. At a second stage of synthesis scheme 602, a second intermediate chemical compound (e.g., characterized by chemical structure 512) can be formed by reacting the first intermediate chemical compound 508 with DMPA. In various embodiments, the second stage of synthesis scheme 602 can be facilitated by alkylation reaction conditions or coupling reaction conditions. Further, at a third stage of the synthesis scheme 602 the functionalized cyclic carbonate monomers characterized by the first cyclic carbonate chemical structure 102 can be achieve by reacting the second intermediate chemical compound (e.g., characterized by chemical structure 512) with the carbonyl equivalent compound 513 triphosgene. In various embodiments, the third stage of synthesis scheme 602 can be facilitated by carbonate reaction conditions.

The resulting functionalized cyclic carbonate monomer 604 can comprise a linking group comprising a four carbon alkyl chain with an oxygen end group facilitating a bond with the aryl halide group, wherein the linking group couples the aryl halide group to the carbonate molecular backbone. As shown in FIG. 6, an ester group can form as a result of the covalently bonding between the aryl halide group and the linkage group. Further, synthesis scheme 602 exemplifies that the functional group of the aryl halide compound can facilitate the bonding with the linkage chemical compound. For instance, in synthesis scheme 502, the oxygen end group of the linkage group is derived from the hydroxyl functional group of the aryl halide compound. In various embodiments, the functionalized cyclic carbonate monomer 604 can comprise an ester group that is electron withdrawing and can facilitate activation of the halide (e.g., fluorine) towards displacement in one or more subsequent nucleophilic aromatic substitutions.

Also depicted in FIG. 6, synthesis of the one or more functionalized cyclic carbonate monomers characterized by the first cyclic carbonate chemical structure 102 can further comprise one or more stages that modify the first intermediate chemical compound prior to formation of the second intermediate compound. For example, synthesis scheme 606 can be employed to form functionalized cyclic carbonate monomer 608. A first intermediate chemical compound 508 can be formed at the first stage of synthesis scheme 606 by reacting a linkage chemical compound characterized by chemical structure 404 with an aryl halide compound characterized by chemical structure 410. In various embodiments, the first stage of synthesis scheme 606 can be facilitated by alkylation reaction conditions or coupling reaction conditions. Further, the first intermediate chemical compound 508 can be modified at a second stage of synthesis scheme 606 to replace the non-bonded end group derived form the linkage chemical compound (e.g., the hydroxyl group) with a new functional group, such as a methane sulfonyl group (e.g., represented by "OMs"). For example, the first intermediate chemical compound can be reacted with one or more activating reagents 607 to facilitate the modification. Example activating reagents 607 can include, but are not limited to: p-tolylsulfonyl chloride (e.g., as depicted in FIG. 6), methansulfonyl chloride, trifluoromethane sulfonic anhydride, trifluoroacetic anhydride, a combination thereof, and/or the like. In various embodiments, the second stage of synthesis scheme 606 can be facilitated by alkylation reaction conditions or coupling reaction conditions. Subsequently, the second intermediate chemical compound (e.g., characterized by chemical structure 512) can be formed at a third stage of synthesis scheme 606 by reacting the modified first intermediate chemical compound 609 with DMPA. In various embodiments, the third stage of synthesis scheme 606 can be facilitated by alkylation reaction conditions or coupling reaction conditions. Further, at a fourth stage of the synthesis scheme 606 the functionalized cyclic carbonate monomer 608 characterized by the first cyclic carbonate chemical structure 102 can be achieved by reacting the second intermediate chemical compound (e.g., characterized by chemical structure 512) with the carbonyl equivalent compound 513 triphosgene. In various embodiments, the fourth stage of the synthesis scheme 606 can be facilitated by the carbonate reaction conditions.

The resulting functionalized cyclic carbonate monomer 608 can comprise a linking group comprising a two carbon alkyl chain with a nitrogen end group facilitating a bond with the aryl halide group, wherein the linking group couples the aryl halide group to the carbonate molecular backbone. Further, synthesis scheme 606 exemplifies that the end group derived from the one or more linkage chemical compounds can facilitate the bonding with the aryl halide compound. For instance, in synthesis scheme 606, the amino end group of the linkage group is derived from the amino end group of the linkage chemical compound. In various embodiments, the functionalized cyclic carbonate monomer 608 can comprise a sulfonyl group that is electron withdrawing and can facilitate activation of the halide (e.g., fluorine) towards displacement in one or more subsequent nucleophilic aromatic substitutions.

Synthesis scheme 610 can be employed to form functionalized cyclic carbonate monomer 612. A first intermediate chemical compound 508 can be formed at the first stage of synthesis scheme 610 by reacting a linkage chemical compound characterized by chemical structure 406 with an aryl halide compound characterized by chemical structure 414. In various embodiments, the first stage of synthesis scheme 610 can be facilitated by the alkylation reaction conditions or the coupling reaction conditions. Further, the first intermediate chemical compound 508 can be modified at a second stage of synthesis scheme 610 to replace the non-bonded end group derived form the linkage chemical compound (e.g., the hydroxyl group) with a new functional group. For example, the first intermediate chemical compound 508 can be reacted with activating reagent 607 tolylsulfonyl chloride to facilitate the modification. In various embodiments, the second stage of synthesis scheme 610 can be facilitated by the alkylation reaction conditions or the coupling reaction conditions. Subsequently, the second intermediate chemical compound (e.g., characterized by chemical structure 512) can be formed at a third stage of synthesis scheme 610 by reacting the modified first intermediate chemical compound 609 with DMPA. In various embodiments, the third stage of synthesis scheme 610 can be facilitated by the alkylation reaction conditions or the coupling reaction conditions. Further, at a fourth stage of the synthesis scheme 610 the functionalized cyclic carbonate monomers characterized by the first cyclic carbonate chemical structure 102 can be achieve by reacting the second intermediate chemical compound (e.g., characterized by chemical structure 512) with carbonyl equivalent compound 513 triphosgene. In various embodiments, fourth stage of synthesis scheme 610 can be facilitated by the carbonate reaction conditions.

The resulting functionalized cyclic carbonate monomer 612 can comprise a linking group comprising a two carbon alkyl chain with an oxygen end group facilitating a bond with the aryl halide group, wherein the linking group couples the aryl halide group to the molecular backbone. As shown in FIG. 6, an ester group can form as a result of the covalently bonding between the aryl halide group and the linkage group. Further, synthesis scheme 610 exemplifies that the functional group of the aryl halide compound can facilitate the bonding with the linkage chemical compound. For instance, in synthesis scheme 610, the oxygen end group of the linkage group is derived from the hydroxyl functional group of the aryl halide compound. In various embodiments, the functionalized cyclic carbonate monomer 612 can comprise an ester group that is electron withdrawing and can facilitate activation of the halide (e.g., fluorine) towards displacement in one or more subsequent nucleophilic aromatic substitutions.

Synthesis scheme 614 can be employed to form functionalized cyclic carbonate monomer 616. A first intermediate chemical compound 508 can be formed at the first stage of synthesis scheme 614 by reacting a linkage chemical compound characterized by chemical structure 404 with an aryl halide compound characterized by chemical structure 412. In various embodiments, the first stage of synthesis scheme 614 can be facilitated by alkylation reaction conditions or coupling reaction conditions. Further, the first intermediate chemical compound 508 can be modified at a second stage of synthesis scheme 614 to replace the non-bonded end group derived form the linkage chemical compound (e.g., the hydroxyl group) with a new functional group, such as methane sulfonyl group (e.g., represented by "OMs"). For example, the first intermediate chemical compound 508 can be reacted with activating reagent 607 tolylsulfonyl chloride to facilitate the modification. In various embodiments, the second stage of synthesis scheme 614 can be facilitated by alkylation reaction conditions or coupling reaction conditions. Subsequently, the second intermediate chemical compound (e.g., characterized by chemical structure 512) can be formed at a third stage of synthesis scheme 614 by reacting the modified first intermediate chemical compound 609 with DMPA. In various embodiments, the third stage of synthesis scheme 614 can be facilitated by alkylation reaction conditions or coupling reaction conditions. Further, at a fourth stage of the synthesis scheme 614 the functionalized cyclic carbonate monomers characterized by the first cyclic carbonate chemical structure 102 can be achieve by reacting the second intermediate chemical compound (e.g., characterized by chemical structure 512) with carbonyl equivalent compound 513 triphosgene. In various embodiments, fourth stage of synthesis scheme 614 can be facilitated by the carbonate reaction conditions.

The resulting functionalized cyclic carbonate monomer 616 can comprise a linking group comprising a two carbon alkyl chain with a nitrogen end group facilitating a bond with the aryl halide group, wherein the linking group couples the aryl halide group to the molecular backbone. Further, synthesis scheme 614 exemplifies that the end group derived from the one or more linkage chemical compounds can facilitate the bonding with the aryl halide compound. For instance, in synthesis scheme 614, the amino end group of the linkage group is derived from the amino end group of the linkage chemical compound. In various embodiments, the functionalized cyclic carbonate monomer 616 can comprise a sulfonyl group that is electron withdrawing and can facilitate activation of the halide (e.g., fluorine) towards displacement in one or more subsequent nucleophilic aromatic substitutions.

Synthesis scheme 618 can be employed to form functionalized cyclic carbonate monomer 620. For example, a first stage of synthesis scheme 618 can form a first intermediate chemical compound 508 by reacting a linkage chemical compound characterized by chemical structure 406 with an aryl halide compound characterized by chemical structure 416. In various embodiments, the first stage of synthesis scheme 618 can be facilitated by the alkylation reaction conditions or the coupling reaction conditions. At a second stage of synthesis scheme 618, a second intermediate chemical compound (e.g., characterized by chemical structure 512) can be formed by reacting the first intermediate chemical compound 508 with DMPA. In various embodiments, the second stage of synthesis scheme 618 can be facilitated by the alkylation reaction conditions or the coupling reaction conditions. Further, at a third stage of the synthesis scheme 618 the functionalized cyclic carbonate monomer 620 characterized by the first cyclic carbonate chemical structure 102 can be achieve by reacting the second intermediate chemical compound (e.g., characterized by chemical structure 512) with the carbonyl equivalent compound 513 triphosgene. In various embodiments, fourth stage of synthesis scheme 618 can be facilitated by the carbonate reaction conditions.

The resulting functionalized cyclic carbonate monomer 620 can comprise a linking group comprising a two carbon alkyl chain with an oxygen end group facilitating a bond with the aryl halide group, wherein the linking group couples the aryl halide group to the molecular backbone. As shown in FIG. 6, an ester group can form as a result of the covalently bonding between the aryl halide group and the linkage group. Further, synthesis scheme 618 exemplifies that the functional group of the aryl halide compound can facilitate the bonding with the linkage chemical compound. For instance, in synthesis scheme 618, the oxygen end group of the linkage group is derived from the hydroxyl functional group of the aryl halide compound. In various embodiments, the functionalized cyclic carbonate monomer 620 can comprise an ester group that is electron withdrawing and can facilitate activation of the halide (e.g., fluorine) towards displacement in one or more subsequent nucleophilic aromatic substitutions.

Synthesis scheme 622 can be employed to form functionalized cyclic carbonate monomer 624. A first intermediate chemical compound 508 can be formed at the first stage of synthesis scheme 622 by reacting a linkage chemical compound characterized by chemical structure 404 with an aryl halide compound characterized by chemical structure 416. In various embodiments, the first stage of synthesis scheme 622 can be facilitated by alkylation reaction conditions or coupling reaction conditions. Further, the first intermediate chemical compound 508 can be modified at a second stage of synthesis scheme 622 to replace the non-bonded end group derived form the linkage chemical compound (e.g., the hydroxyl group) with a new functional group, such as methane sulfonyl group (e.g., represented by "OMs"). For example, the first intermediate chemical compound 508 can be reacted with activating reagent 607 tolylsulfonyl chloride to facilitate the modification. In various embodiments, the second stage of synthesis scheme 622 can be facilitated by alkylation reaction conditions or coupling reaction conditions. Subsequently, the second intermediate chemical compound (e.g., characterized by chemical structure 512) can be formed at a third stage of synthesis scheme 622 by reacting the modified first intermediate chemical compound 609 with DMPA. In various embodiments, the third stage of synthesis scheme 622 can be facilitated by alkylation reaction conditions or coupling reaction conditions. Further, at a fourth stage of the synthesis scheme 622 the functionalized cyclic carbonate monomer 624 characterized by the first cyclic carbonate chemical structure 102 can be achieve by reacting the second intermediate chemical compound (e.g., characterized by chemical structure 512) with the carbonyl equivalent compound 513 triphosgene. In various embodiments, fourth stage of synthesis scheme 622 can be facilitated by the carbonate reaction conditions.

The resulting functionalized cyclic carbonate monomer 624 can comprise a linking group comprising a two carbon alkyl chain with a nitrogen end group facilitating a bond with the aryl halide group, wherein the linking group couples the aryl halide group to the molecular backbone. Further, synthesis scheme 622 exemplifies that the end group derived from the one or more linkage chemical compounds can facilitate the bonding with the aryl halide compound. For instance, in synthesis scheme 622, the amino end group of the linkage group is derived from the amino end group of the linkage chemical compound. In various embodiments, the functionalized cyclic carbonate monomer 624 can comprise an amino group that is electron withdrawing and can facilitate activation of the halide (e.g., fluorine) towards displacement in one or more subsequent nucleophilic aromatic substitutions.

Synthesis scheme 626 can be employed to form functionalized cyclic carbonate monomer 628. A first intermediate chemical compound 508 can be formed at the first stage of synthesis scheme 626 by reacting a linkage chemical compound characterized by chemical structure 404 with an aryl halide compound characterized by chemical structure 414. In various embodiments, the first stage of synthesis scheme 626 can be facilitated by alkylation reaction conditions or coupling reaction conditions. Further, the first intermediate chemical compound 508 can be modified at a second stage of synthesis scheme 626 to replace the non-bonded end group derived form the linkage chemical compound (e.g., the hydroxyl group) with a new functional group. For example, the first intermediate chemical compound 508 can be reacted with activating reagent 607 tolylsulfonyl chloride to facilitate the modification. In various embodiments, second stage of synthesis scheme 626 can be facilitated by alkylation reaction conditions or coupling reaction conditions. Subsequently, the second intermediate chemical compound (e.g., characterized by chemical structure 512) can be formed at a third stage of synthesis scheme 626 by reacting the modified first intermediate chemical compound 609 with DMPA. In various embodiments, third stage of synthesis scheme 626 can be facilitated by alkylation reaction conditions or coupling reaction conditions. Further, at a fourth stage of the synthesis scheme 626 the functionalized cyclic carbonate monomers characterized by the first cyclic carbonate chemical structure 102 can be achieve by reacting the second intermediate chemical compound (e.g., characterized by chemical structure 512) with the carbonyl equivalent compound 513 triphosgene. In various embodiments, fourth stage of synthesis scheme 622 can be facilitated by the carbonate reaction conditions.

The resulting functionalized cyclic carbonate monomer 628 can comprise a linking group comprising a two carbon alkyl chain with a nitrogen end group facilitating a bond with the aryl halide group, wherein the linking group couples the aryl halide group to the molecular backbone. Further, synthesis scheme 626 exemplifies that the end group derived from the one or more linkage chemical compounds can facilitate the bonding with the aryl halide compound. For instance, in synthesis scheme 626, the amino end group of the linkage group is derived from the amino end group of the linkage chemical compound. In various embodiments, the functionalized cyclic carbonate monomer 628 can comprise an amino group that is electron withdrawing and can facilitate activation of the halide (e.g., fluorine) towards displacement in one or more subsequent nucleophilic aromatic substitutions.

Figure 7:
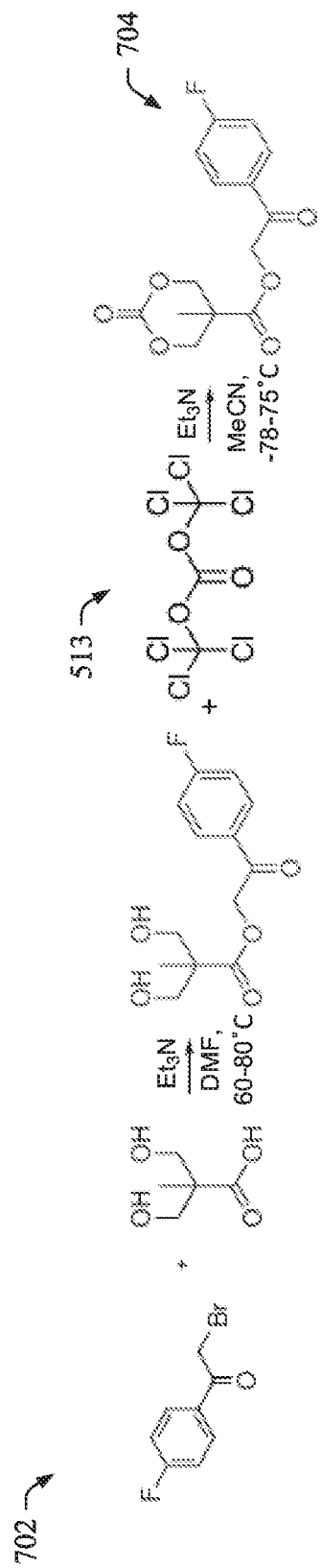
FIG. 7 illustrates a diagram of an example, non-limiting synthesis scheme that can characterize the synthesis of a functionalized cyclic carbonate monomer in accordance with one or more embodiments described herein.

FIG. 7 illustrates a diagram of an example, non-limiting synthesis scheme 702 that can exemplify formation of one or more functionalized cyclic carbonate monomers characterized by the first cyclic carbonate chemical structure 102 in accordance with one or more embodiments described herein. Repetitive description of like elements employed in other embodiments described herein is omitted for sake of brevity. In various embodiments, exemplary synthesis scheme 702 can exemplify the features of synthesis scheme 502 and method 300.

Synthesis scheme 702 exemplifies that the one or more functionalized cyclic carbonate monomers characterized by the first cyclic carbonate chemical structure 102 can be formed without a linkage chemical compound. For example, the one or more aryl halide compounds can be directly reacted with a chemical compound characterized by chemical structure 510, such as DMPA to form the functionalized monomer compound characterized by chemical structure 512. At a first stage of the synthesis scheme 702, an aryl halide compound characterized by chemical structure 414 can be reacted with DMPA to form a functionalized monomer compound (e.g., characterized by chemical structure 512). As shown in FIG. 7, n various embodiments, the first stage of synthesis scheme 702 can be facilitated by the alkylation reaction conditions. At a second stage of the synthesis scheme 702, the functionalized monomer compound (e.g., characterized by chemical structure 512) can be reacted with the carbonyl equivalent compound 513 triphosgene to achieve functionalized cyclic carbonate monomer 704 characterized by the first cyclic carbonate chemical structure 102. As shown in FIG. 7, n various embodiments the second stage of synthesis scheme 702 can be facilitated by the carbonate reaction conditions. The resulting functionalized cyclic carbonate monomer 704 can comprise a linkage group comprising one carbon atom, which can be derived from the functional group of the aryl halide compound. In various embodiments, the functionalized cyclic carbonate monomer 704 can comprise a ketone group that is electron withdrawing and can facilitate activation of the halide (e.g., fluorine) towards displacement in one or more subsequent nucleophilic aromatic substitutions.

Figure 8:
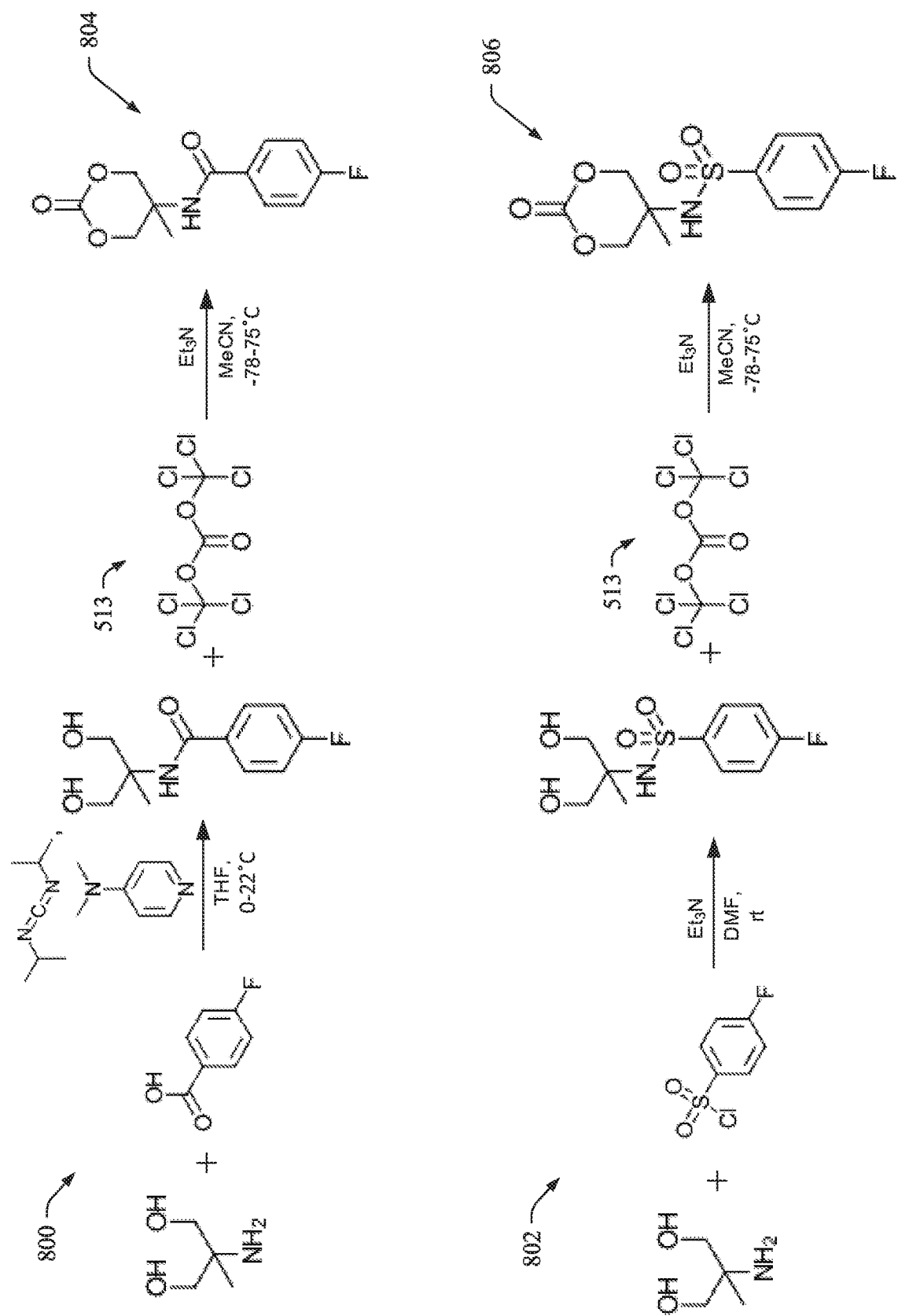
FIG. 8 illustrates a diagram of example, non-limiting synthesis schemes that can characterize the synthesis of a functionalized cyclic carbonate monomer in accordance with one or more embodiments described herein.

FIG. 8 illustrates a diagram of example, non-limiting synthesis schemes 800 and 802 that can exemplify formation of one or more functionalized cyclic carbonate monomers characterized by the third cyclic carbonate chemical structure 106 in accordance with one or more embodiments described herein. Repetitive description of like elements employed in other embodiments described herein is omitted for sake of brevity. In various embodiments, exemplary synthesis schemes 800 and 802 can exemplify the features of synthesis scheme 504 and method 300.

At a first stage of synthesis scheme 800 the one or more aryl halide compounds characterized by chemical structure 414 can be directly reacted with a chemical compound characterized by chemical structure 514 to form a functionalized monomer compound characterized by chemical structure 516. As shown in FIG. 8, in various embodiments the first stage of synthesis scheme 800 can be facilitated by the coupling reaction conditions. At a second stage of the synthesis scheme 800, the functionalized monomer compound characterized by chemical structure 514 can be reacted with the carbonyl equivalent compound 513 triphosgene to achieve functionalized cyclic carbonate monomer 804 characterized by the third cyclic carbonate chemical structure 106. In various embodiments, the second stage of synthesis scheme 800 can be facilitated by the carbonate reaction conditions. In various embodiments, the resulting functionalized cyclic carbonate monomer 804 can comprise an amino group that is electron withdrawing and can facilitate activation of the halide (e.g., fluorine) towards displacement in one or more subsequent nucleophilic aromatic substitutions.

At a first stage of synthesis scheme 802 the one or more aryl halide compounds characterized by chemical structure 410 can be directly reacted with a chemical compound characterized by chemical structure 514 to form a functionalized monomer compound characterized by chemical structure 516. As shown in FIG. 8, in various embodiments the first stage of synthesis scheme 802 can be facilitated by the alkylation reaction conditions. At a second stage of the synthesis scheme 802, the functionalized monomer compound characterized by chemical structure 514 can be reacted with the carbonyl equivalent compound 513 triphosgene to achieve functionalized cyclic carbonate monomer 806 characterized by the third cyclic carbonate chemical structure 106. In various embodiments, second stage of synthesis scheme 802 can be facilitated by the carbonate reaction conditions. In one or more embodiments, the resulting functionalized cyclic carbonate monomer 806 can comprise an sulfonyl group that is electron withdrawing and can facilitate activation of the halide (e.g., fluorine) towards displacement in one or more subsequent nucleophilic aromatic substitutions.

Figure 9:
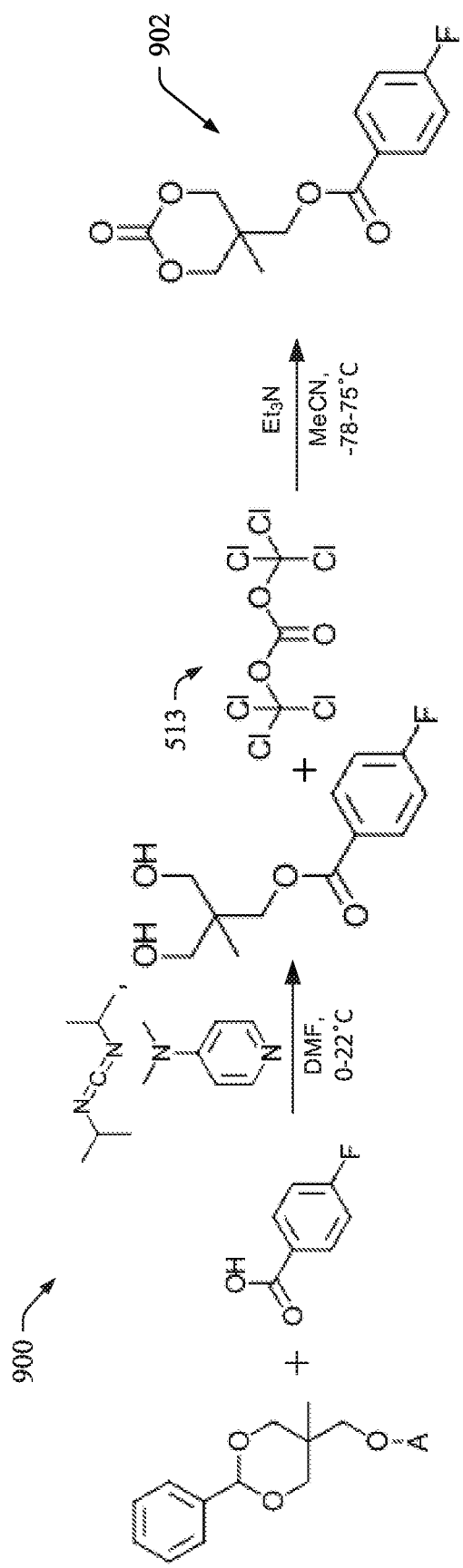
FIG. 9 illustrates a diagram of an example, non-limiting synthesis scheme that can characterize the synthesis of a functionalized cyclic carbonate monomer in accordance with one or more embodiments described herein.

FIG. 9 illustrates a diagram of example, non-limiting synthesis scheme 900 that can exemplify formation of one or more functionalized cyclic carbonate monomers characterized by the second cyclic carbonate chemical structure 104 in accordance with one or more embodiments described herein. Repetitive description of like elements employed in other embodiments described herein is omitted for sake of brevity. In various embodiments, exemplary synthesis scheme 900 can exemplify the features of synthesis scheme 506 and method 300.

At a first stage of synthesis scheme 900 the one or more aryl halide compounds characterized by chemical structure 414 can be directly reacted with a chemical compound characterized by chemical structure 518 to form the functionalized monomer compound characterized by chemical structure 520. As shown in FIG. 9, in various embodiments the first stage of synthesis scheme 900 can be facilitated by the coupling reaction conditions. At a second stage of the synthesis scheme 900, the functionalized monomer compound characterized by chemical structure 520 can be reacted with the carbonyl equivalent compound 513 triphosgene to achieve functionalized cyclic carbonate monomer 902 characterized by the second cyclic carbonate chemical structure 104. As shown in FIG. 9, in various embodiments the second stage of synthesis scheme 900 can be facilitated by the carbonate reaction conditions. In one or more embodiments, the resulting functionalized cyclic carbonate monomer 902 can comprise an ester group that is electron withdrawing and can facilitate activation of the halide (e.g., fluorine) towards displacement in one or more subsequent nucleophilic aromatic substitutions.

Figure 10:
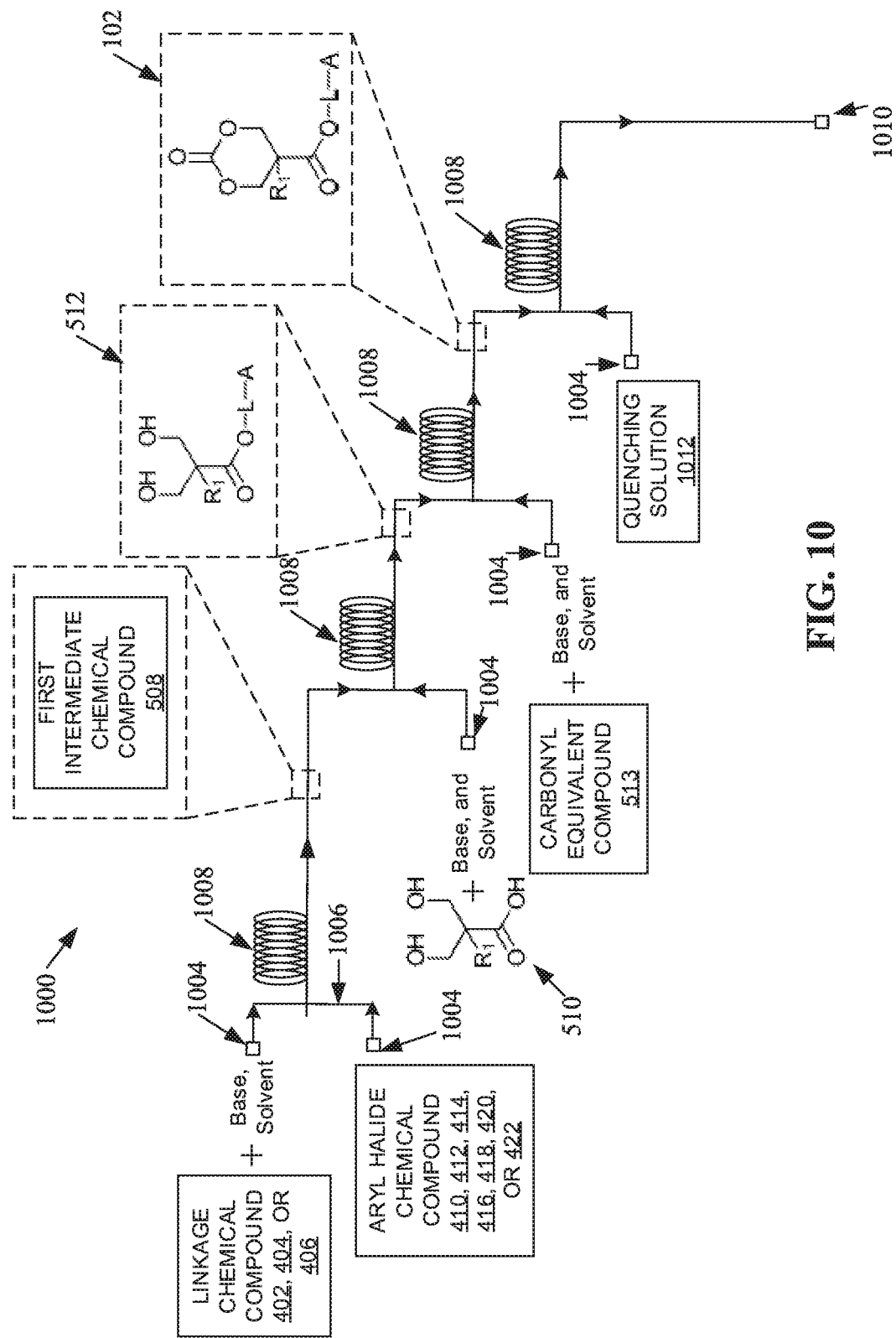
FIG. 10 illustrates a diagram of an example, non-limiting flow reactor system that can facilitate one or more synthesis schemes of functionalized cyclic carbonate monomers in accordance with one or more embodiments described herein.

FIG. 10 illustrates a diagram of an example, non-limiting flow reactor system 1000 that can facilitate synthesis of the one or more functionalized cyclic carbonate monomers characterized by the first cyclic carbonate chemical structure 102, the second cyclic carbonate chemical structure 104, and/or the third cyclic carbonate chemical structure 106 in accordance with one or more embodiments described herein. Repetitive description of like elements employed in other embodiments described herein is omitted for sake of brevity. For example, FIG. 10 depicts the flow reactor system 1000 employed to facilitate synthesis scheme 500.

The flow reactor system 1000 can comprise, for example, one or more inlets 1004, one or more channels 1006, one or more reactor loops 1008, and/or one or more outlets 1010. The one or more channels 1006 can extend from the one or more inlets 1004 to the one or more outlets 1010. The one or more channels 1006 (e.g., microfluidic channels) can comprise, for example: tubes (e.g., microfluidic tubes), pipes, joiners (e.g., T-mixers), a combination thereof, and/or the like. Additionally, the one or more channels 1006 can be oriented into one or more reactor loops 1008 at one or more stages between the one or more inlets 1004 and/or the one or more outlets 1010. The one or more reactor loops 1008 can influence the length of the flow reactor system 1000 and thereby the residence time of the one or more synthesis reactions. One of ordinary skill in the art will recognize that the number of loops comprising the reactor loops 1008 and/or the dimensions of the loops can vary depending on a desired flow rate, residence time, and/or turbulence. Further, while the reactor loops 1008 are depicted in FIG. 10 as characterized by circular shaped structures, the architecture of the reactor loops 608 is not so limited. For example, the one or more reactor loops 1008 can be characterized by elliptical and/or polygonal shaped structures.

FIG. 10 exemplifies the features of the flow reactor system 1000 with regards to synthesis scheme 500. In accordance with synthesis scheme 500, the one or more aryl halide compounds (e.g., characterized by chemical structure 410, 412, 414, 416, 418, 420, or 422) can enter the one or more flow reactor system 1000 via one or more first inlets 1004, while the one or more linkage chemical compounds (e.g., characterized by chemical structure 402, 404, or 406) can enter the one or more flow reactor system 1000 via one or more second inlets 1004. Further, one or more bases and/or solvents employed in the alkylation reaction conditions or coupling reaction conditions can also enter the flow reactor system 1000 via the first or second inlets 1004 to facilitate the first stage of synthesis scheme 500 within the flow reactor system 1000. The one or more aryl halide compounds can meet and/or mix with the one or more linkage chemical compounds within the one or more channels 1006; thereby forming a stream of chemical reactants. As the stream flows through the one or more channels 1006, the first intermediate chemical compound 508 can be formed (e.g., as delineated by the dashed lines shown in FIG. 10).

Additionally, the first intermediate chemical compound 508 can flow downstream through the one or more channels 1006 and mix with a chemical compound characterized by chemical structure 510 to form a second intermediate chemical compound characterized by chemical structure 512. For example, the chemical compound characterized by chemical structure 510 can enter the flow reactor system 1000 via one or more third inlets 1004. Further, one or more bases and/or solvents employed in the alkylation reaction conditions or coupling reaction conditions can also enter the flow reactor system 1000 via the third inlet 1004 to facilitate the second stage of synthesis scheme 500 within the flow reactor system 1000. Further, an additional set of reactor loops 1008 can facilitate the formation reaction of the second intermediate chemical compound characterized by chemical structure 512 (e.g., as delineated by the dashed lines shown in FIG. 10).

Additionally, the second intermediate chemical compound characterized by chemical structure 512 can flow downstream through the one or more channels 1006 and mix with the one or more carbonyl equivalent compounds 513 to facilitate a reaction that forms a functionalized cyclic carbonate monomer characterized by the first cyclic carbonate chemical structure 102. For example, the one or more carbonyl equivalent compounds 513 can enter the flow reactor system 1000 via one or more fourth inlets 1004. Further, one or more bases and/or solvents employed in the carbonate reaction conditions can also enter the flow reactor system 1000 via the fourth inlets 1004 to facilitate the third stage of synthesis scheme 500 within the flow reactor system 1000. Moreover, an additional set of reactor loops 1008 can facilitate the formation reaction of the resulting functionalized cyclic carbonate monomer. As the stream flows through the one or more channels 1006 and/or the third set of reactor loops 1008, the functionalized cyclic carbonate monomer characterized by the first cyclic carbonate chemical structure 102 can be formed (e.g., as delineated by the dashed lines shown in FIG. 10). In one or more embodiments, a quenching solution 1012 can be further introduced into the flow reactor system 1000 via a fifth inlet 1004 to quench the chemical reaction that is facilitated by the carbonate reaction conditions and forms the functionalized cyclic monomer characterized by the first cyclic carbonate chemical structure 102. For example, the quenching solution 1012 can comprise hydrochloric acid.

Further, the one or more synthesis reactions described herein to form the one or more functionalized cyclic carbonate monomers characterized by first cyclic carbonate chemical structure 102 can be performed within one or more embodiments of the flow reactor system 1000, and/or can be characterized by residence times within the flow reactor system 1000 ranging from, for example, greater than or equal to 0.001 seconds (s) and less than or equal to 1800 s. Further, each of the respective inlets 1004 can be controlled independently of the other inlets 1004. Therefore, respective chemicals can be introduced into the one or more flow reactors system 1000 at respective quantities, speeds, and/or pressures. Additionally, one of ordinary skill in the art will recognize that the flow reactor system 1000 can be expanded or contracted to facilitate the reaction conditions of the various synthesis reactions (e.g., the flow reactor system 1000 can be employed with additional or fewer reactor loops 1008, inlets 1004, and/or channels 1006).

Figure 11:
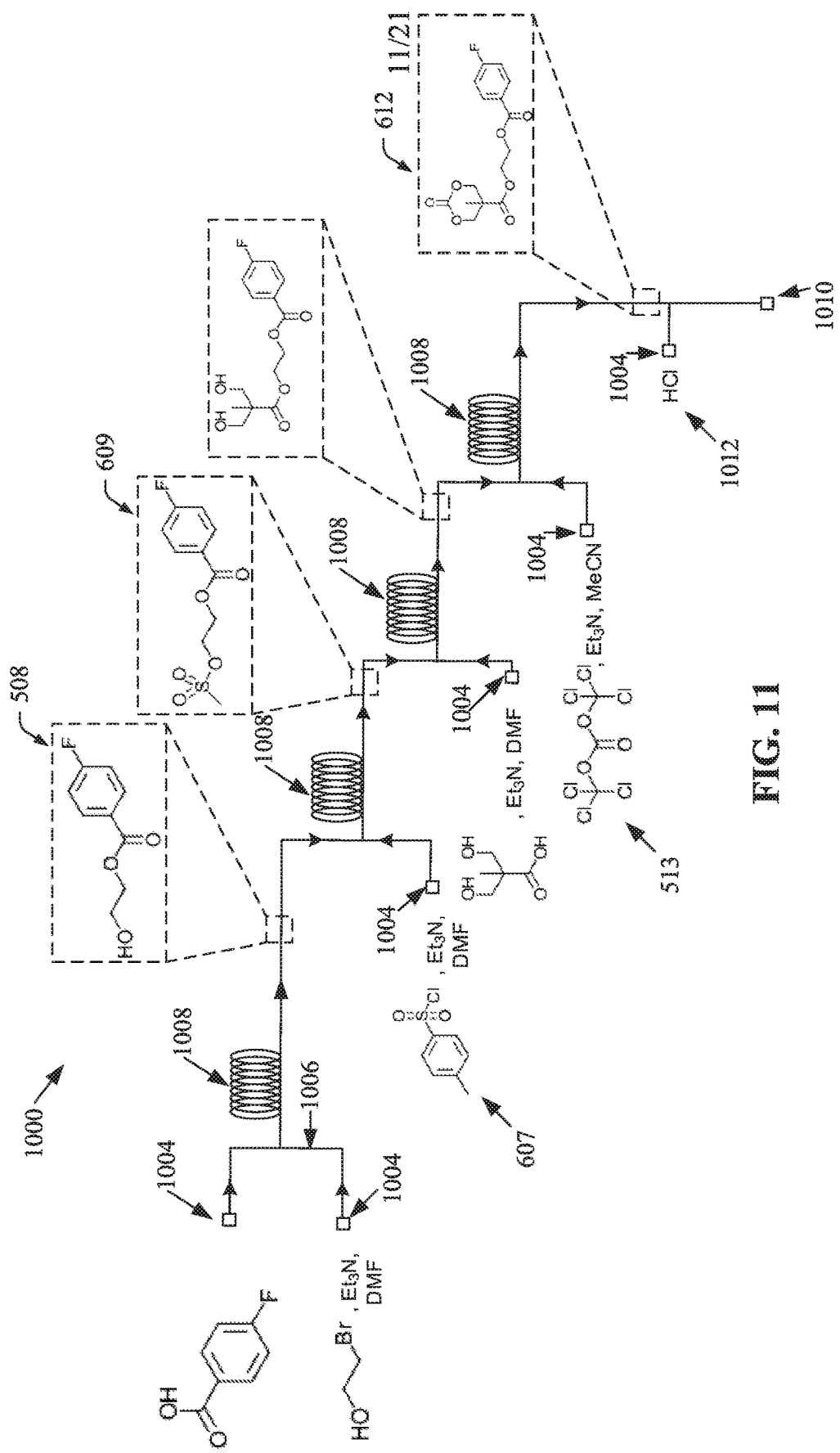
FIG. 11 illustrates a diagram of an example, non-limiting functionalized carbonate monomer synthesis scheme that can be performed within one or more flow reactor systems in accordance with one or more embodiments described herein.

FIG. 11 illustrates a diagram of the example, non-limiting flow reactor system 1000 with regards to example synthesis scheme 610 in accordance with one or more embodiments described herein. Repetitive description of like elements employed in other embodiments described herein is omitted for sake of brevity.

In accordance with synthesis scheme 610, the one or more aryl halide compounds (e.g., characterized by chemical structure 414) can enter the one or more flow reactor system 1000 via one or more first inlets 1004, while the one or more linkage chemical compounds (e.g., characterized by chemical structure 406) can enter the one or more flow reactor system 1000 via one or more second inlets 1004. Further, one or more bases (e.g., $Et_3N$) and/or solvents (e.g., DMF) employed in the alkylation reaction conditions can also enter the flow reactor system 1000 via the first or second inlets 1004 to facilitate the first stage of synthesis scheme 610 within the flow reactor system 1000. The one or more aryl halide compounds can meet and/or mix with the one or more linkage chemical compounds within the one or more channels 1006; thereby forming a stream of chemical reactants. As the stream flows through the one or more channels 1006, the first intermediate chemical compound 508 can be formed (e.g., as delineated by the dashed lines shown in FIG. 11).

Additionally, the first intermediate chemical compound can flow downstream through the one or more channels 1006 and mix with the activating reagent 607 tolylsulfonyl chloride to facilitate a reaction that modifies the intermediate chemical compound 508. For example, the activating reagent 607 can enter the flow reactor system 1000 via one or more third inlets 1004. Further, one or more bases (e.g., $Et_3N$) and/or solvents (e.g., DMF) employed in the alkylation reaction conditions can also enter the flow reactor system 1000 via the third inlet 1004 to facilitate the second stage of synthesis scheme 610 within the flow reactor system 1000. Moreover, an additional set of reactor loops 1008 can facilitate the modification reaction of the intermediate chemical compound 508. As the stream flows through the one or more channels 1006 and/or the second set of reactor loops 1008, the modified first intermediate chemical compound 609 can be formed (e.g., as delineated by the dashed lines shown in FIG. 10).

Additionally, the modified first intermediate chemical compound 609 can flow downstream through the one or more channels 1006 and mix with DMPA to facilitate a reaction that forms the second intermediate chemical compound characterized by chemical structure 512. For example, the DMPA can enter the flow reactor system 1000 via one or more fourth inlets 1004. Further, one or more bases (e.g., $Et_3N$) and/or solvents (e.g., DMF) employed in the alkylation reaction conditions can also enter the flow reactor system 1000 via the fourth inlets 1004 to facilitate the third stage of synthesis scheme 610 within the flow reactor system 1000. Further, an additional set of reactor loops 1008 can facilitate the formation of the second intermediate chemical compound characterized by chemical structure 512. As the stream flows through the one or more channels 1006 and/or the third set of reactor loops 1008, the second intermediate chemical compound characterized by chemical structure 512 can be formed (e.g., as delineated by the dashed lines shown in FIG. 11).

Additionally, the second intermediate chemical compound can flow downstream through the one or more channels 1006 and mix with the carbonyl equivalent compound 513 triphosgene to facilitate a reaction that forms the functionalized cyclic carbonate monomer 612. For example, the carbonyl equivalent compound 513 triphosgene can enter the flow reactor system 1000 via one or more fifth inlets 1004. Further, one or more bases (e.g., $Et_3N$) and/or solvents (e.g., MeCN) employed in the carbonate reaction conditions can also enter the flow reactor system 1000 via the fifth inlets 1004 to facilitate the fourth stage of synthesis scheme 610 within the flow reactor system 1000 As the stream flows through the one or more channels 1006 and/or the fourth set of reactor loops 1008, the functionalized cyclic carbonate monomer 612 can be formed (e.g., as delineated by the dashed lines shown in FIG. 11). In one or more embodiments, a quenching solution 1012 of hydrochloric acid can be further introduced into the flow reactor system 1000 via a fourth inlet 1004 to quench the chemical reaction that is facilitated by the carbonate reaction conditions and forms the functionalized cyclic carbonate monomer characterized by the third cyclic carbonate chemical structure 106.

Figure 12:
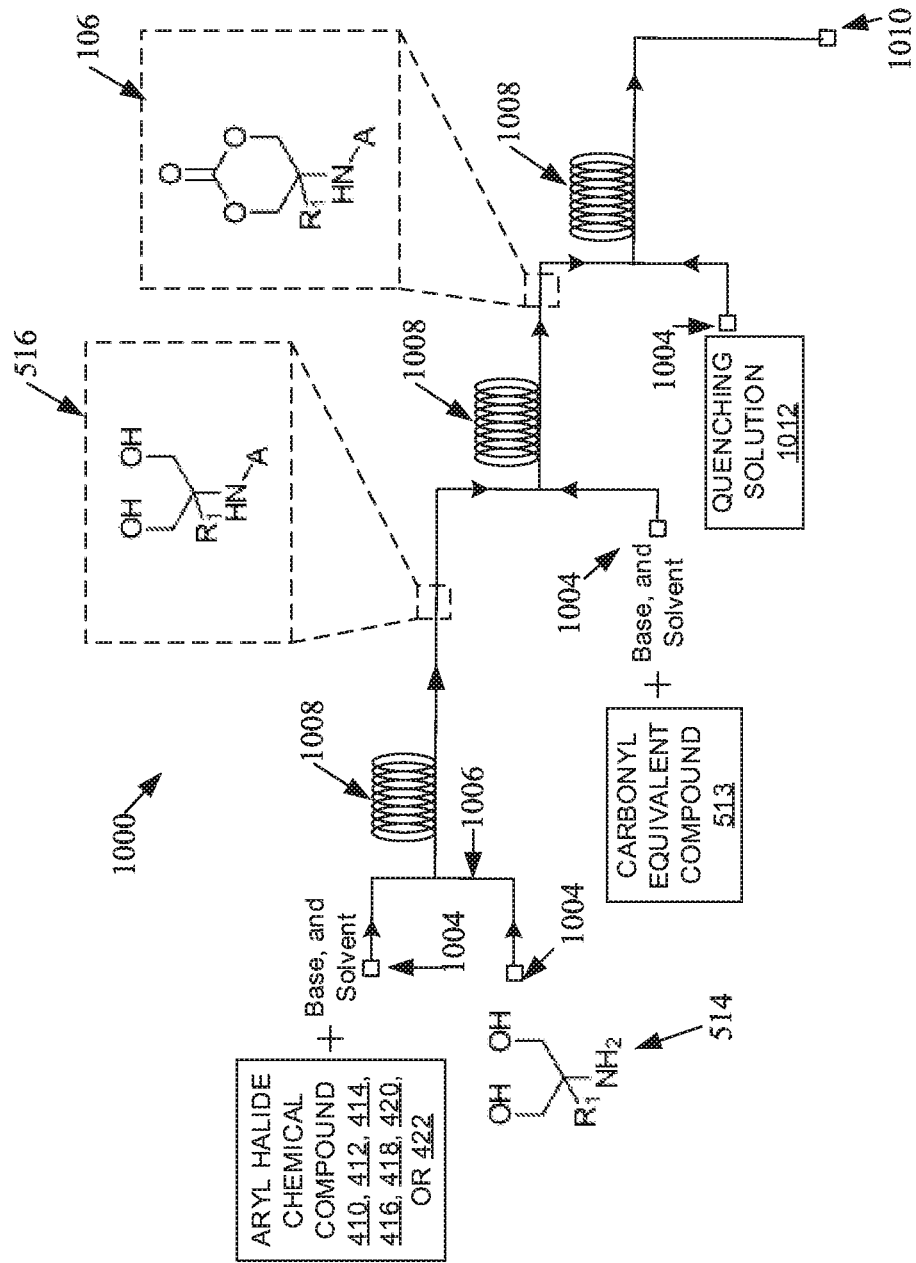
FIG. 12 illustrates a diagram of an example, non-limiting functionalized carbonate monomer synthesis scheme that can be performed within one or more flow reactor systems in accordance with one or more embodiments described herein.

FIG. 12 illustrates a diagram of the example, non-limiting flow reactor system 1000 with regards to synthesis scheme 504 in accordance with one or more embodiments described herein. Repetitive description of like elements employed in other embodiments described herein is omitted for sake of brevity. In accordance with synthesis scheme 504, one or more aryl halide compounds (e.g., characterized by chemical structure 410, 412, 414, 416, 418, 420, or 422) can enter the one or more flow reactor system 1000 via one or more first inlets 1004, while the one or more chemical compounds characterized by chemical structure 514 can enter the one or more flow reactor system 1000 via one or more second inlets 1004. Further, one or more bases and/or solvents employed in the alkylation reaction conditions or coupling reaction conditions can also enter the flow reactor system 1000 via the first or second inlets 1004 to facilitate the first stage of synthesis scheme 504 within the flow reactor system 1000. The one or more aryl halide compounds characterized by chemical structure 410, 412, 414, 416, 418, 420, or 422 can meet and/or mix with the one or more chemical compounds characterized by chemical structure 514 within the one or more channels 1006; thereby forming a stream of chemical reactants. As the stream flows through the one or more channels 1006, an intermediate chemical compound characterized by chemical structure 516 can be formed (e.g., as delineated by the dashed lines shown in FIG. 12).

Additionally, the intermediate chemical compound characterized by chemical structure 516 can flow downstream through the one or more channels 1006 and mix with the one or more carbonyl equivalent compounds 513 to facilitate a reaction that forms a functionalized cyclic carbonate monomer characterized by the third cyclic carbonate chemical structure 106. For example, the one or more carbonyl equivalent compounds 513 can enter the flow reactor system 1000 via one or more third inlets 1004. Further, one or more bases and/or solvents employed in the carbonate reaction conditions can also enter the flow reactor system 1000 via the third inlet 1004 to facilitate the second stage of synthesis scheme 504 within the flow reactor system 1000. As the stream flows through the one or more channels 1006 and/or the second set of reactor loops 1008, the functionalized cyclic carbonate monomer characterized by the third cyclic carbonate chemical structure 106 can be formed (e.g., as delineated by the dashed lines shown in FIG. 12). In one or more embodiments, the quenching solution 1012 can be further introduced into the flow reactor system 1000 via a fourth inlet 1004 to quench the chemical reaction that is facilitated by the carbonate reaction conditions and forms the functionalized cyclic monomer characterized by the third cyclic carbonate chemical structure 106.

Figure 13:
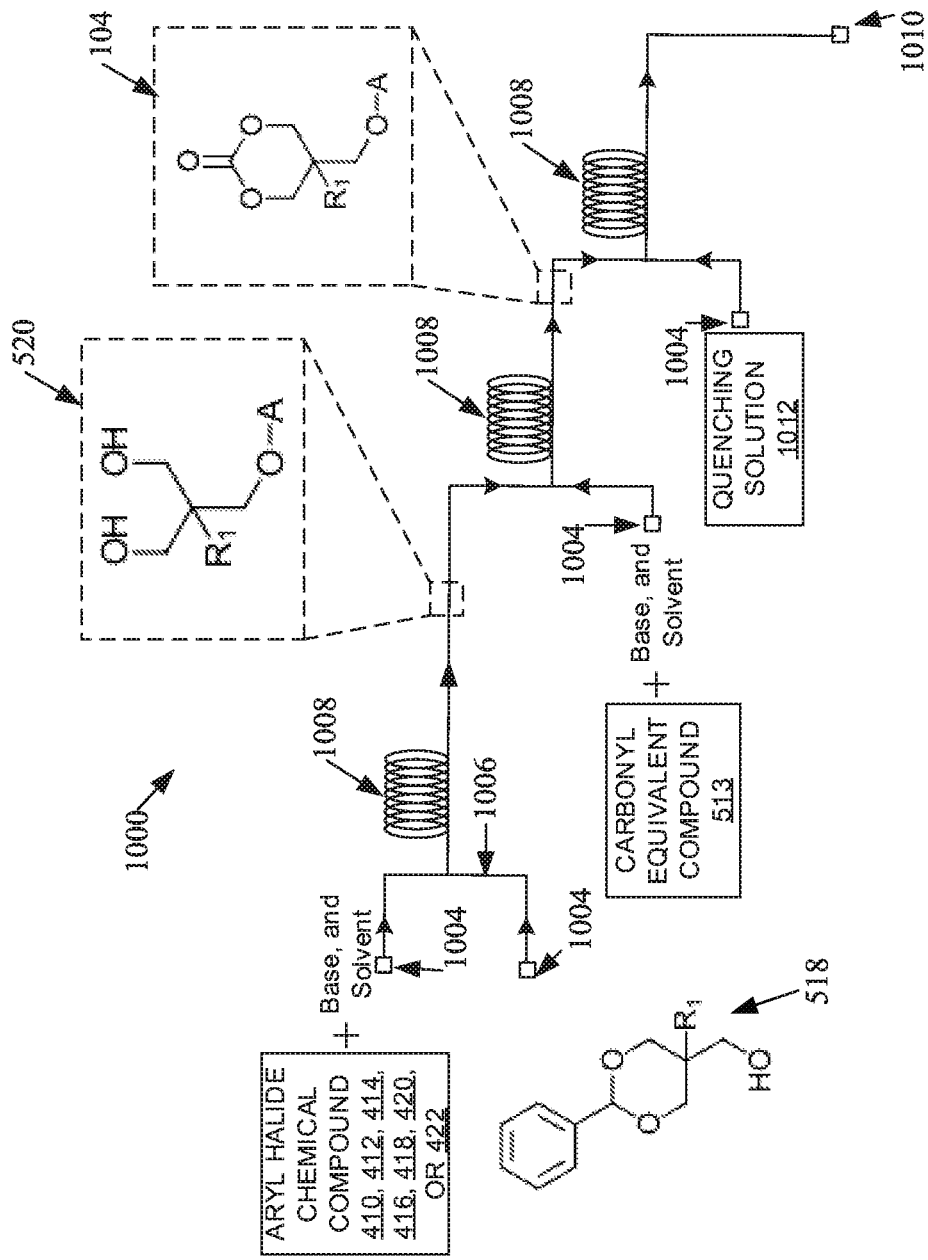
FIG. 13 illustrates a diagram of an example, non-limiting functionalized carbonate monomer synthesis scheme that can be performed within one or more flow reactor systems in accordance with one or more embodiments described herein.

FIG. 13 illustrates a diagram of the example, non-limiting flow reactor system 1000 with regards to synthesis scheme 506 in accordance with one or more embodiments described herein. Repetitive description of like elements employed in other embodiments described herein is omitted for sake of brevity. In accordance with synthesis scheme 506, one or more aryl halide compounds (e.g., characterized by chemical structure 410, 412, 414, 416, 418, 420, or 422) can enter the one or more flow reactor system 1000 via one or more first inlets 1004, while the one or more chemical compounds characterized by chemical structure 518 can enter the one or more flow reactor system 1000 via one or more second inlets 1004. Further, one or more bases and/or solvents employed in the alkylation reaction conditions or coupling reaction conditions can also enter the flow reactor system 1000 via the first or second inlets 1004 to facilitate the first stage of synthesis scheme 506 within the flow reactor system 1000 The one or more aryl halide compounds characterized by chemical structure 410, 412, 414, 416, 418, 420, or 422 can meet and/or mix with the one or more chemical compounds characterized by chemical structure 518 within the one or more channels 1006; thereby forming a stream of chemical reactants. As the stream flows through the one or more channels 1006, an intermediate chemical compound characterized by chemical structure 520 can be formed (e.g., as delineated by the dashed lines shown in FIG. 13).

Additionally, the intermediate chemical compound characterized by chemical structure 520 can flow downstream through the one or more channels 1006 and mix with one or more carbonyl equivalent compounds 513 to facilitate a reaction that forms a functionalized cyclic carbonate monomer characterized by the second cyclic carbonate chemical structure 104. For example, the one or more carbonyl equivalent compounds 513 can enter the flow reactor system 1000 via one or more third inlets 1004. Further, one or more bases and/or solvents employed in the carbonate reaction conditions can also enter the flow reactor system 1000 via the third inlet 1004 to facilitate the second stage of synthesis scheme 506 within the flow reactor system 1000. As the stream flows through the one or more channels 1006 and/or the second set of reactor loops 1008, the functionalized cyclic carbonate monomer characterized by the second cyclic carbonate chemical structure 104 can be formed (e.g., as delineated by the dashed lines shown in FIG. 13). In one or more embodiments, a quenching solution 1012 of hydrochloric acid can be further introduced into the flow reactor system 1000 via a fourth inlet 1004 to quench the chemical reaction that is facilitated by the carbonate reaction conditions and forms the functionalized cyclic carbonate monomer characterized by the second cyclic carbonate chemical structure 104.

FIG. 14 illustrates a diagram of example, non-limiting first polycarbonate chemical structure 1402, second polycarbonate chemical structure 1404, and/or third polycarbonate chemical structure 1406 that can characterize one or more functionalized polycarbonate polymers in accordance with one or more embodiments described herein. Repetitive description of like elements employed in other embodiments described herein is omitted for sake of brevity. In various embodiments, the polycarbonate polymers characterized by the first polycarbonate chemical structure 1402, the second polycarbonate chemical structure 1404, and/or the third polycarbonate chemical structure 1406 can be polymerized from the one or more functionalized cyclic carbonate monomers characterized by the first cyclic carbonate chemical structure 102, the second cyclic carbonate chemical structure 104, the third cyclic carbonate chemical structure 106.

As described herein, "$R_1$" can represent the first functional group comprising an alkyl group having greater than or equal to one carbon atom and less than or equal to three carbon atoms. Example alkyl groups that can be represented by "$R_1$" can include, but are not limited: a methyl group, an ethyl group, a propyl group, etc., and/or the like. Also, "$R_2$" can represent a second functional group comprising one or more of the following groups: an alcohol group, an alkyl group having from 1 to 20 carbon atoms, a benylic alcohol, an allylic alcohol, a propargylic alcohol, a group derived from a macromonomer, a combination thereof, and/or the like.

Also shown in FIG. 14, the first polycarbonate chemical structure 1402 can comprise one or more handle functional groups (e.g., represented by "$A_1$") can be covalently bonded to a molecular backbone of the polycarbonate via the one or more linkage groups (e.g., represented by "L"). As described herein, in various embodiments, the one or more linkage groups (e.g., represented by "L") can comprise an alkyl chain having greater than or equal to one carbon atom and less than or equal to 20 carbon atoms. Further, the one or more linkage groups (e.g., represented by "L") can comprise one or more end groups that include, for example, an oxygen or nitrogen atom bonded to the one or more handle functional groups (e.g., represented by "$A_1$") and/or the polycarbonate molecular backbone. The second polycarbonate chemical structure 1404 can comprise the one or more handle functional groups (e.g., represented by "$A_1$") directly bonded to the polycarbonate molecular backbone. Similarly, the third polycarbonate chemical structure 1406 can comprise the one or more handle functional groups (e.g., represented by "$A_1$") directly bonded to the polycarbonate molecular backbone.

In one or more embodiments, the one or more handle functional groups (e.g., represented by "$A_1$") can be modified embodiments of the aryl halide groups depicted in FIG. 1 (e.g., represented by "A") such that at least one halide atom is replaced with a further bond to the one or more third functional groups (e.g., represented by "$R_3$") via a sulfur atom. One or more example handle functional group structures 1408 are also shown in FIG. 14, wherein the "*" can delineate a connection to the one or more linkage groups (e.g., represented by "L"), the polycarbonate molecular backbone, or a connection to one or more sulfur atoms (e.g., in accordance with the first poly carbonate chemical structure 1402, the second poly carbonate chemical structure 1404, and/or the third polycarbonate chemical structure 1406). Further, "X" can represent a halide (e.g., a fluorine atom, a chloride atom, a bromine atom, or an iodine atom). In one or more embodiments, "X" can represent a fluorine atom. Further, "Y" can represent an oxygen atom, —NH—, or a sulfur atom. Additionally, "n" can represent an integer greater than or equal to 1 and less than or equal to 8, and "m" can represent an integer greater than or equal to 2 and less than or equal to 5,000. In various embodiments, "$R_3$" can represent a third functional group comprising: an alkyl group, aromatic group, heteroaromatic group, pendent ether groups, thioether groups, alkyl halide groups, phosphonate groups, epoxide groups, sulfonate groups, urea groups, thiourea groups, guanidinium groups, carbamate groups, ester groups, and carbonate groups, a combination thereof, and/or the like.

FIG. 15 illustrates a flow diagram of an example, non-limiting method 1500 that can facilitate polymerizing a polycarbonate compound and modifying the polycarbonate compound post polymerization to achieve a polycarbonate polymer characterized by the first polycarbonate chemical structure 1402, the second polycarbonate chemical structure 1404, the third polycarbonate chemical structure 1406 in accordance with one or more embodiments described herein. Repetitive description of like elements employed in other embodiments described herein is omitted for sake of brevity.

At 1502, the method 1500 can comprise performing, via a flow reactor (e.g., flow reactor system 1000), one or more ROPs of one or more cyclic carbonate monomers to form one or more polycarbonate polymers, wherein the one or more cyclic carbonate monomers comprise one or more aryl halide groups. For example, the one or more cyclic carbonate monomers can be characterized by the first cyclic carbonate chemical structure 102, the second cyclic carbonate chemical structure 104, and/or the third cyclic carbonate chemical structure 106. In various embodiments, the one or more ROPs at 1502 can be facilitated by one or more initiators and/or anionic catalysts. Example initiators than can be employed to facilitate the one or more ROPs can include, but are not limited to: a primary alcohol, an amine, a thiol, a carbanion, a combination thereof, and/or the like.

At 1504, the method 1500 can comprise reacting the one or more polycarbonate polymers with one or more silyl protected thiols, wherein the silyl protected thiols comprise a target functional group that covalently bonds to the aryl halide group. One of ordinary skill in the art will recognize, that the silyl group of the silyl protected thiols can comprise alkyl chains of various lengths. For example, the silyl group can be a trimethylsilyl, a triethylsilyl, a triisopropylsilyl, etc., a combination thereof, and/or the like. Further, the aryl halide group can serve as a handle functional group that can facilitate post polymerization functionalization of the polycarbonate polymers with the one or more target functional groups of the silyl protected thiols. For instance, the modification reaction facilitated by the reacting at 1504 can be a nucleophilic aromatic substitution, wherein the aryl halide group of the polycarbonate polymer formed at 1502 can comprise one or more electron withdrawing groups that can activate the one or more halides to be displaced by the sulfur atom of the one or more TMSS compounds. In one or more embodiments, the reacting at 1504 can be performed via batch reaction chemistry. Alternatively, in one or more embodiments, the reacting at 1504 can be performed in a continuous flow reaction via the flow reactor (e.g., flow reactor system 1000). For instance, the flow rate associated with the one or more ROPs at 1502 can be set to match the flow rate associated with the modification reaction at 1504.

In one or more embodiments, the reacting at 1504 can be facilitated by one or more catalysts and/or solvents. Example catalysts that can facilitate the reacting at 1504 can include, but are not limited to: DBU, DBU.OBz, BzOK, BzONa, potassium acetate, potassium hexanoate, sodium acetate, a combination thereof, and/or the like. Example solvents that can facilitate the reacting at 1504 can include, but are not limited to: NMP, DMF, acetonitrile, DMSO, THF, ethyl acetate, ethylene carbonate, a combination thereof, and/or the like. In various embodiments, method 1500 can be performed at room temperature.

Figure 16:
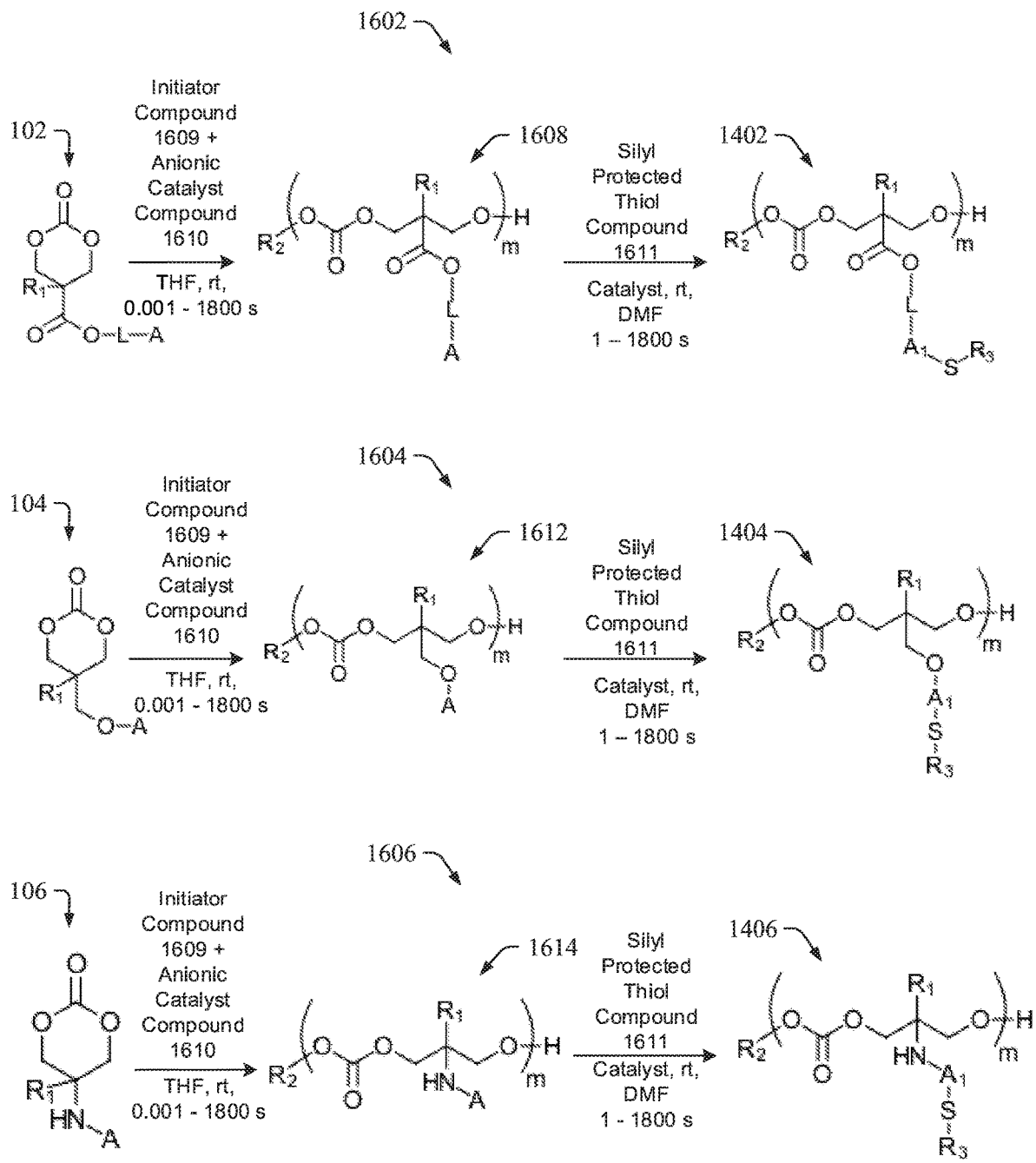
FIG. 16 illustrates a diagram of example, non-limiting polymerization schemes that can characterize polymerization and/or post polymerization modification of one or more functionalized polycarbonate polymers in accordance with one or more embodiments described herein.

FIG. 16 illustrates a diagram of example, non-limiting polymerization scheme 1602, 1604, and 1606 that can characterize the synthesis of one or more polycarbonate polymers that can be characterized, respectively, by the first polycarbonate chemical structure 1402, the second polycarbonate chemical structure 1404, the third polycarbonate chemical structure 1406 in accordance with one or more embodiments described herein. Repetitive description of like elements employed in other embodiments described herein is omitted for sake of brevity. As shown in FIG. 16, "m" can be an integer greater than or equal to 2 and less than or equal to 5000.

Polymerization scheme 1602 exemplifies that the one or more polycarbonate polymers characterized by the first polycarbonate chemical structure 1402 can be polymerized from the one or more cyclic carbonate monomers characterized by first cyclic carbonate chemical structure 102. For example, a first stage of the polymerization scheme 1602 can comprise one or more ROPs that can form a polycarbonate platform chemical structure 1608. In various embodiments, the one or more cyclic carbonate monomers characterized by first cyclic carbonate chemical structure 102 can be reacted with the one or more initiator compounds 1609 and/or anionic catalyst compounds 1610 described herein (e.g., with regards to method 1500) to facilitate the one or more ROPs. For example, the one or more initiator compounds 1609 can include, but are not limited to: a primary alcohol, an amine, a thiol, a carbanion, a combination thereof, and/or the like. Additionally, in various embodiments the one or more anionic catalyst compounds 1610 (e.g., employed in the various polymerizations and/or methods described herein) can be the anionic catalysts disclosed in the inventor's U.S. patent application Ser. No. 16/028,989 and U.S. patent application Ser. No. 16/029,025, which are incorporated in their entirety herein by this reference. During the one or more ROPs; the first functional group (e.g., represented by "$R_1$") can be derived from the one or more cyclic carbonate monomers, and the second functional group (e.g., represented by "$R_2$") can be derived from the one or more initiator compounds 1609. In various embodiments, the one or more initiator compounds 1609 and/or anionic catalyst compounds 1610 can be supplied with one or more solvents (e.g., THF), and the one or more ROPs can be performed at room temperature.

At a second stage of the polymerization scheme 1602, the polycarbonate platform chemical structure 1608 can be further reacted with one or more silyl protected thiol compounds 1611. The one or more silyl protected thiol can comprise one or more silyl groups comprising one or more alkyl chains. Example silyl groups can include, but are not limited to: trimethylsilyl, a triethylsilyl, a triisopropylsilyl, etc., a combination thereof, and/or the like. For example, the one or more silyl protected thiol compounds 1611 can be characterized by the following chemical structure:

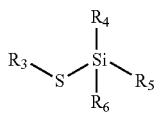

Wherein "$R_3$" represents a third functional group that can be the target for functionalization with the polycarbonate platform chemical structure 1608. In various embodiments, the modification reaction performed at the second stage can be facilitated by one or more catalysts described herein (e.g., with regards to method 1500) to facilitate one or more nucleophilic aromatic substitutions. Additionally, "$R_4$", "$R_5$", and/or "$R_6$" can respectively represent functional groups that can comprise alkyl groups, such as methyl, ethyl groups, propyl groups, etc., a combination thereof, and/or the like. In one or more embodiments, the "$R_4$", "$R_5$", and/or "$R_6$" can have the same chemical structure or different chemical structures. For instance, in various embodiments the silyl protected thiol compound 1611 can be a trimethylsilyl protect thiol ("TMSS") compound. In various embodiments, the silyl protected thiol compound 1611 can covalently bond to the aryl halide group (e.g., represented by "A") of the polycarbonate platform chemical structure 1608, such that at least one halide of the aryl halide group is replaced by a covalent bonding with a sulfur atom of the silyl protected thiol compound 1611; thereby, forming the handle functional group (e.g., represented by "$A_1$") and functionalizing the polycarbonate platform chemical structure 1608 with the one or more third functional groups (e.g., represented by "$R_3$") bonded to the sulfur atom and derived from the silyl protected thiol compound 1611.

In various embodiments, polymerization scheme 1602 can be employed within a flow chemistry procedure (e.g., employed within one or more flow reactor systems 1000). For example, introduction of the one or more silyl protected thiol compounds 1611 and/or solvents at the second stage of polymerization scheme 1602 into the stream of chemical reactants characterized by the polycarbonate platform chemical structure 1608 can quench the chemical reaction initiated at the first stage of polymerization scheme 1602. Further, one or more byproducts of the quenching can further catalyze the modification reaction of the second stage of the polymerization scheme 1602 (e.g., catalyze the functionalization of the aryl halide group with the silyl protected thiol compound 1611).

Polymerization scheme 1604 exemplifies that the one or more polycarbonate polymers characterized by the second polycarbonate chemical structure 1404 can be polymerized from the one or more cyclic carbonate monomers characterized by second cyclic carbonate chemical structure 104. For example, a first stage of the polymerization scheme 1604 can comprise one or more ROPs that can form a second polycarbonate platform chemical structure 1612. In various embodiments, the one or more cyclic carbonate monomers characterized by second cyclic carbonate chemical structure 104 can be reacted with the one or more initiator compounds 1609 and/or anionic catalyst compounds 1610 described herein (e.g., with regards to method 1500) to facilitate the one or more ROPs. During the one or more ROPs; the first functional group (e.g., represented by "$R_1$") can be derived from the one or more cyclic carbonate monomers, and the second functional group (e.g., represented by "$R_2$") can be derived from the one or more initiator compounds 1609. In various embodiments, the one or more initiator compounds 1609 and/or anionic catalyst compounds 1610 can be supplied with one or more solvents (e.g., THF), and the one or more ROPs can be performed at room temperature.

At a second stage of the polymerization scheme 1604, the second polycarbonate platform chemical structure 1612 can be further reacted with the one or more silyl protected thiol compounds 1611 (e.g., TMSS). In various embodiments, the modification reaction performed at the second stage can be facilitated by one or more catalysts described herein (e.g., with regards to method 1500) to facilitate one or more nucleophilic aromatic substitutions. In various embodiments, the silyl protected thiol compound 1611 can covalently bond to the aryl halide group (e.g., represented by "A") of the second polycarbonate platform chemical structure 1612, such that at least one halide of the aryl halide group is replaced by a covalent bonding with a sulfur atom of the silyl protected thiol compound 1611; thereby, forming the handle functional group (e.g., represented by "$A_1$") and functionalizing the second polycarbonate platform chemical structure 1612 with the one or more third functional groups (e.g., represented by "$R_3$") bonded to the sulfur atom and derived from the silyl protected thiol compound 1611.

In various embodiments, polymerization scheme 1604 can be employed within a flow chemistry procedure (e.g., employed within one or more flow reactor systems 1000). For example, introduction of the one or more silyl protected thiol compounds 1611 and/or solvents at the second stage of polymerization scheme 1604 into the stream of chemical reactants characterized by the second polycarbonate platform chemical structure 1612 can quench the chemical reaction initiated at the first stage of polymerization scheme 1604. Further, one or more byproducts of the quenching can further catalyze the modification reaction of the second stage of the polymerization scheme 1604 (e.g., catalyze the functionalization of the aryl halide group with the silyl protected thiol compound 1611).

Polymerization scheme 1606 exemplifies that the one or more polycarbonate polymers characterized by the third polycarbonate chemical structure 1406 can be polymerized from the one or more cyclic carbonate monomers characterized by third cyclic carbonate chemical structure 106. For example, a first stage of the polymerization scheme 1606 can comprise one or more ROPs that can form a third polycarbonate platform chemical structure 1614. In various embodiments, the one or more cyclic carbonate monomers characterized by third cyclic carbonate chemical structure 106 can be reacted with the one or more initiator compounds 1609 and/or anionic catalyst compounds 1610 described herein (e.g., with regards to method 1500) to facilitate the one or more ROPs. During the one or more ROPs; the first functional group (e.g., represented by "$R_1$") can be derived from the one or more cyclic carbonate monomers, and the second functional group (e.g., represented by "$R_2$") can be derived from the one or more initiator compounds 1609. In various embodiments, the one or more initiator compounds 1609 and/or anionic catalyst compounds 1610 can be supplied with one or more solvents (e.g., THF), and the one or more ROPs can be performed at room temperature.

At a second stage of the polymerization scheme 1606, the third polycarbonate platform chemical structure 1614 can be further reacted with one or more silyl protected thiol compounds 1611. In various embodiments, the modification reaction performed at the second stage can be facilitated by one or more catalysts described herein (e.g., with regards to method 1500) to facilitate one or more nucleophilic aromatic substitutions. In various embodiments, the silyl protected thiol compounds 1611 (e.g., TMSS) can covalently bond to the aryl halide group (e.g., represented by "A") of the third polycarbonate platform chemical structure 1614, such that at least one halide of the aryl halide group is replaced by a covalent bonding with a sulfur atom of the silyl protected thiol compound 1611; thereby, forming the handle functional group (e.g., represented by "$A_1$") and functionalizing the third polycarbonate platform chemical structure 1614 with the one or more third functional groups (e.g., represented by "$R_3$") bonded to the sulfur atom and derived from the silyl protected thiol compound 1611.

In various embodiments, polymerization scheme 1606 can be employed within a flow chemistry procedure (e.g., employed within one or more flow reactor systems 1000). For example, introduction of the one or more silyl protected thiol compounds 1611 and/or solvents at the second stage of polymerization scheme 1606 into the stream of chemical reactants characterized by the third polycarbonate platform chemical structure 1614 can quench the chemical reaction initiated at the first stage of polymerization scheme 1606. Further, one or more byproducts of the quenching can further catalyze the modification reaction of the second stage of the polymerization scheme 1606 (e.g., catalyze the functionalization of the aryl halide group with the silyl protected thiol compound 1611).

Figure 17:
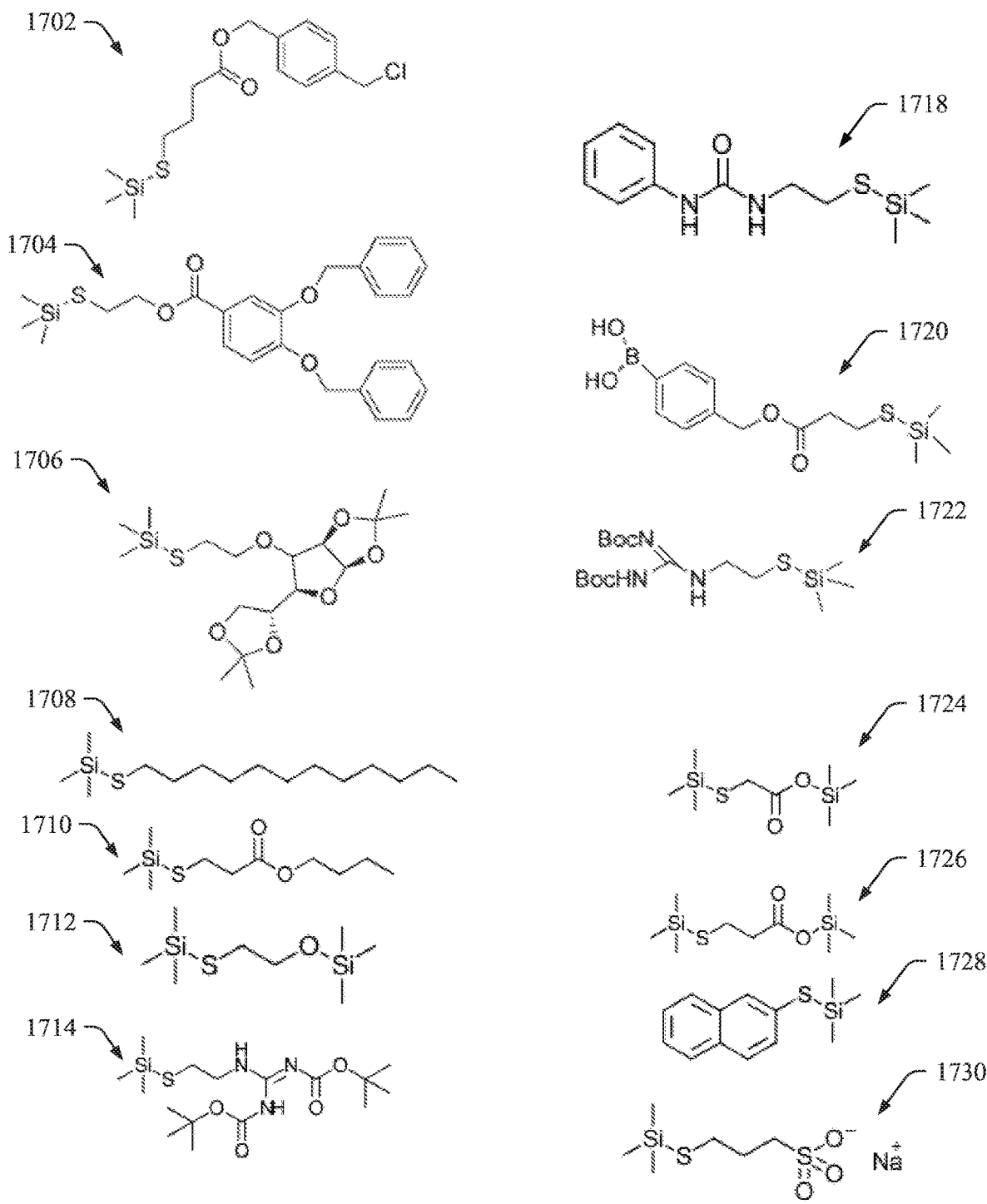
FIG. 17 illustrates a diagram of example, non-limiting chemical structures that can characterize one or more exemplary silyl protected thiol compounds that can be utilized to modify a polycarbonate polymer post polymerization in accordance with one or more embodiments described herein.

FIG. 17 illustrates a diagram of non-limiting, example silyl protected thiol compounds 1611 that can be employed to modify one or more polycarbonate platforms 1608, 1612, and/or 1614 to achieve a polycarbonate polymer characterized by the first polycarbonate chemical structure 1402, the second polycarbonate chemical structure 1404, and/or the third polycarbonate chemical structure 1406 in accordance with one or more embodiments described herein. Repetitive description of like elements employed in other embodiments described herein is omitted for sake of brevity. For instance, example chemical compounds 1702, 1704, 1706, 1708, 1710, 1712, 1714, 1716, 1718, 1720, 1722, 1724, 1726, 1728, 1730 can be employed within the polymerization scheme 1602, 1604, and/or 1606 as the silyl protected thiol compound 1611. As shown in FIG. 17, the one or more example chemical compounds can comprise a trimethylsilyl group bonded to a sulfur atom, which can be bonded to the third functional group. FIG. 17 depicts example functional groups that can be comprised within the one or more silyl protected thiol compounds 1611. One of ordinary skill in the art will recognize that functional groups outside of the examples depicted in FIG. 17 are also envisage in accordance with the various features described herein.

Figure 18:
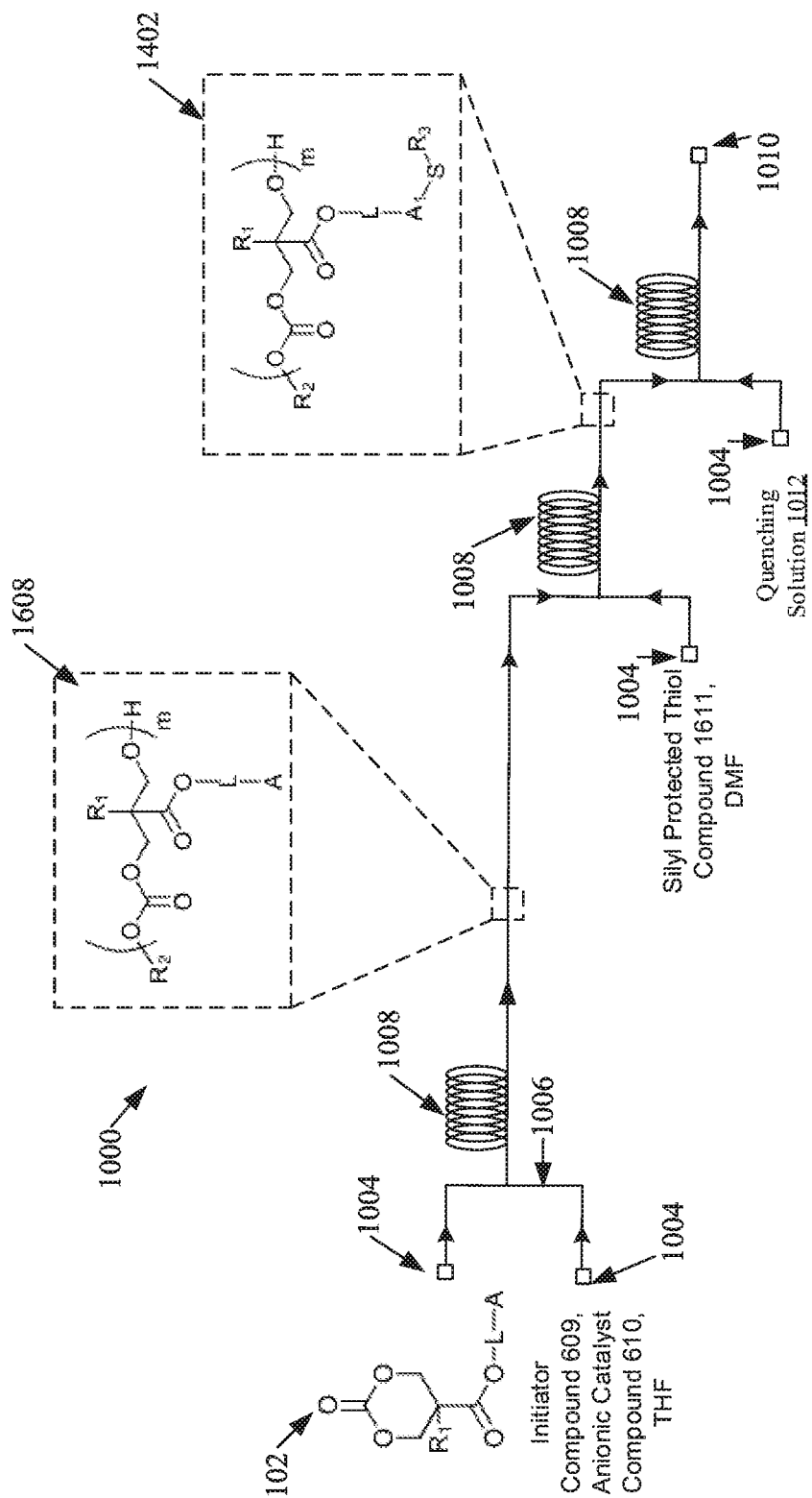
FIG. 18 illustrates a diagram of an example, non-limiting polymerization scheme that can be employed within a flow reactor system to polymerize and/or modify one or more polycarbonate polymers in accordance with one or more embodiments described herein.

FIG. 18 illustrates a diagram of the example, non-limiting polymerization scheme 1602 employed via flow reactor system 1000 in accordance with one or more embodiments described herein. Repetitive description of like elements employed in other embodiments described herein is omitted for sake of brevity. For example, the flow reactor system 1000 can facilitate the polymerization scheme 1602 and/or the various features of method 1500.

In accordance with example polymerization scheme 1602, the one or more functionalized cyclic carbonate monomers characterized by first cyclic carbonate chemical structure 102 can enter the one or more flow reactor system 1000 via one or more first inlets 1004, while the one or more initiator compounds 609 and/or anionic catalyst compounds 610 (e.g., in a solution with a solvent, such as THF) can enter the one or more flow reactor system 1000 via one or more second inlets 1004. For example, the one or more initiator compounds 609 and/or anionic catalyst compounds 610 can be in accordance with the various features described herein with regards to method 1500. The one or more functionalized cyclic carbonate monomers characterized by first cyclic carbonate chemical structure 102 can meet and/or mix with the one or more initiator compounds 609 and/or anionic catalyst compounds 610 within the one or more channels 1006; thereby forming a stream of chemical reactants. As the stream flows through the one or more channels 1006, a polycarbonate platform characterized by the polycarbonate platform chemical structure 1608 can be formed (e.g., as delineated by the dashed lines shown in FIG. 18).

Additionally, the polycarbonate platform characterized by polycarbonate platform chemical structure 1608 can flow downstream through the one or more channels 1006 and mix with the one or more silyl protected thiol compounds 1611 and/or solvents (e.g., DMF) to facilitate a modification reaction that forms a functionalized polycarbonate polymer characterized by first polycarbonate chemical structure 1402. For example, the silyl protected thiol compound 1611 can enter the flow reactor system 1000 via one or more third inlets 1004 (e.g., in a solution with a solvent, such as DMF). In various embodiments, the introduction of the silyl protected thiol compound 1611 and/or the solvent can quench the polymerization reaction and catalyze the subsequent post polymerization modification reaction in flow. Further, the modification reaction can be a post polymerization nucleophilic aromatic substitution reaction facilitated by an additional set of reactor loops 1008. As the stream flows through the one or more channels 1006 and/or the second set of reactor loops 1008, the functionalized polycarbonate polymer characterized by first polycarbonate chemical structure 1402 can be formed (e.g., as delineated by the dashed lines shown in FIG. 18). In one or more embodiments, the quenching solution 1012 (e.g., hydrochloric acid) can be further introduced into the flow reactor system 1000 via a fourth inlet 1004 to quench the post polymerization modification reaction. In one or more embodiments, the one or more ROPs and/or modification reactions can be performed within the flow reactor system 1000 with a residence time that is greater than or equal to 1 and less than or equal to 1800 seconds (s).

While FIG. 18 depicts both the ROP reaction and the post polymerization modification reaction (e.g., nucleophilic aromatic substitution occurring in flow), the architecture of polymerization scheme 1602 is not so limited. For example, in one or more embodiments, the one or more ROPs can be performed in the flow reactor system 1000 (e.g., as shown in FIG. 18), and the resulting polycarbonate platforms characterized by polycarbonate platform chemical structure 1608 can exit the flow reactor system 1000 and be employed in a batch reaction. For instance, the post polymerization nucleophilic aromatic substitution with the silyl protected thiol compound 1611 can be employed via a batch reaction process using one or more catalysts (e.g., DBU, DBU.OBz, BzOK, and/or BzONa).

Figure 19:
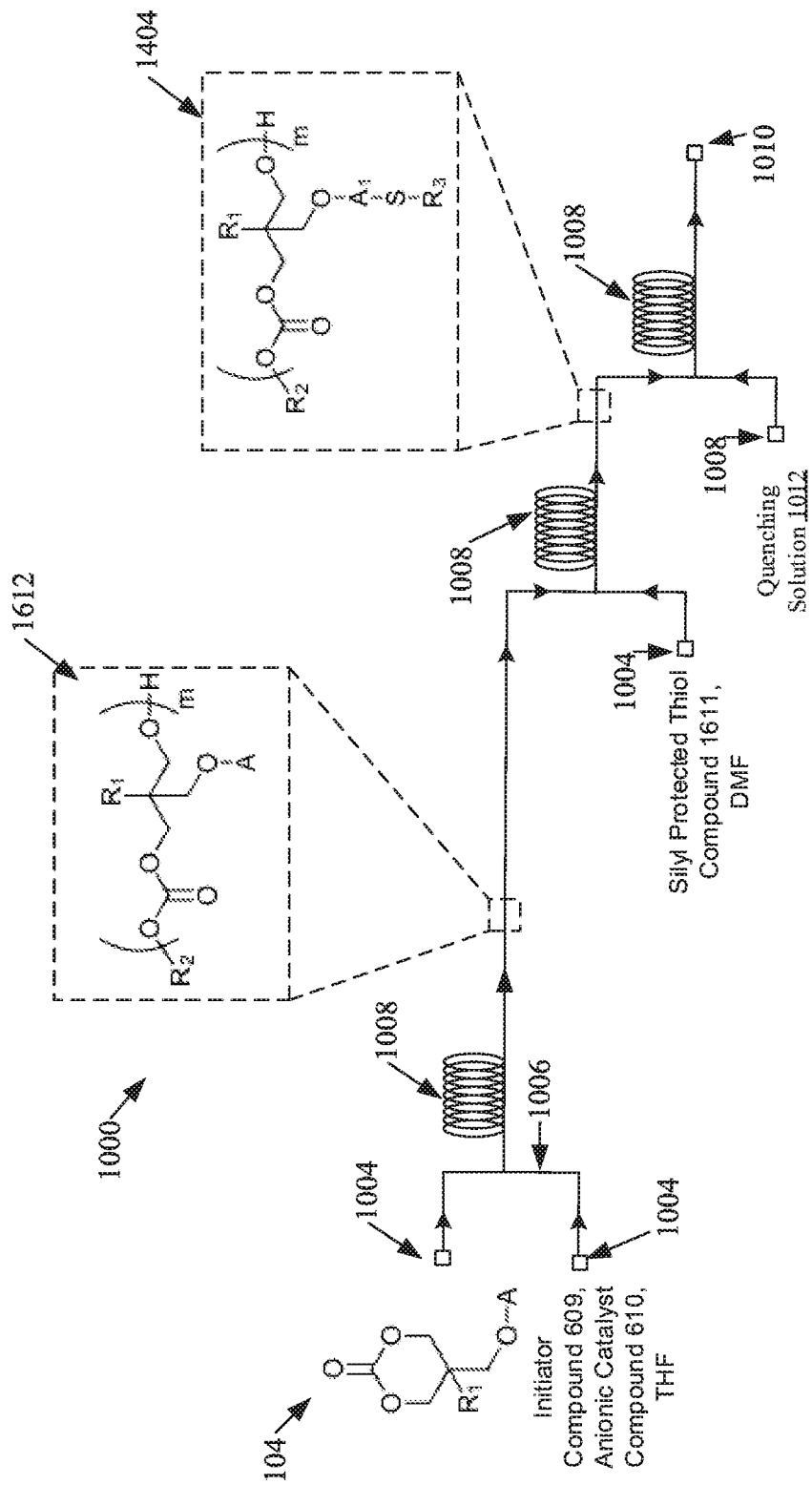
FIG. 19 illustrates a diagram of an example, non-limiting polymerization scheme that can be employed within a flow reactor system to polymerize and/or modify one or more polycarbonate polymers in accordance with one or more embodiments described herein.

FIG. 19 illustrates a diagram of the example, non-limiting polymerization scheme 1604 employed via flow reactor system 1000 in accordance with one or more embodiments described herein. Repetitive description of like elements employed in other embodiments described herein is omitted for sake of brevity. For example, the flow reactor system 1000 can facilitate the polymerization scheme 1604 and/or the various features of method 1500.

In accordance with example polymerization scheme 1604, the one or more functionalized cyclic carbonate monomers characterized by second cyclic carbonate chemical structure 104 can enter the one or more flow reactor system 1000 via one or more first inlets 1004, while the one or more initiator compounds 609 and/or anionic catalyst compounds 610 (e.g., in a solution with a solvent such as THF) can enter the one or more flow reactor system 1000 via one or more second inlets 1004. For example, the one or more initiator compounds 609 and/or anionic catalyst compounds 610 can be in accordance with the various features described herein with regards to method 1500. The one or more functionalized cyclic carbonate monomers characterized by second cyclic carbonate chemical structure 104 can meet and/or mix with the one or more initiator compounds 609 and/or anionic catalyst compounds 610 within the one or more channels 1006; thereby forming a stream of chemical reactants. As the stream flows through the one or more channels 1006, a polycarbonate platform characterized by the second polycarbonate platform chemical structure 1612 can be formed (e.g., as delineated by the dashed lines shown in FIG. 19).

Additionally, the polycarbonate platform characterized by second polycarbonate platform chemical structure 1612 can flow downstream through the one or more channels 1006 and mix with the one or more silyl protected thiol compounds 1611 and/or solvent (e.g., DMF) to facilitate a reaction that forms a functionalized polycarbonate polymer characterized by second polycarbonate chemical structure 1404. For example, the one or more silyl protected thiol compounds 1611 can enter the flow reactor system 1000 via one or more third inlets 1004 (e.g., in a solution with a solvent, such as DMF). In various embodiments, the introduction of the silyl protected thiol compound 1611 and/or the solvent can quench the polymerization reaction and catalyze the subsequent post polymerization modification reaction in flow. Further, the post polymerization modification reaction can be a nucleophilic aromatic substitution reaction, and can be facilitated by an additional set of reactor loops 1008. As the stream flows through the one or more channels 1006 and/or the second set of reactor loops 1008, the functionalized polycarbonate polymer characterized by second polycarbonate chemical structure 1404 can be formed (e.g., as delineated by the dashed lines shown in FIG. 19). In one or more embodiments, the quenching solution 1012 (e.g., hydrochloric acid) can be further introduced into the flow reactor system 1000 via a fourth inlet 1004 to quench the post polymerization modification reaction. In one or more embodiments, the one or more ROPs and/or modification reactions can be performed within the flow reactor system 1000 with a residence time that is greater than or equal to 1 and less than or equal to 1800 s.

While FIG. 19 depicts both the ROP reaction and the post polymerization modification reaction (e.g., nucleophilic aromatic substitution occurring in flow), the architecture of polymerization scheme 1604 is not so limited. For example, in one or more embodiments, the one or more ROPs can be performed in the flow reactor system 1000 (e.g., as shown in FIG. 19), and the resulting polycarbonate platforms characterized by second polycarbonate platform chemical structure 1612 can exit the flow reactor system 1000 and be employed in a batch reaction. For instance, the post polymerization nucleophilic aromatic substitution with the silyl protected thiol compound 1611 can be employed via a batch reaction process using one or more catalysts (e.g., DBU, DBU.OBz, BzOK, and/or BzONa).

Figure 20:
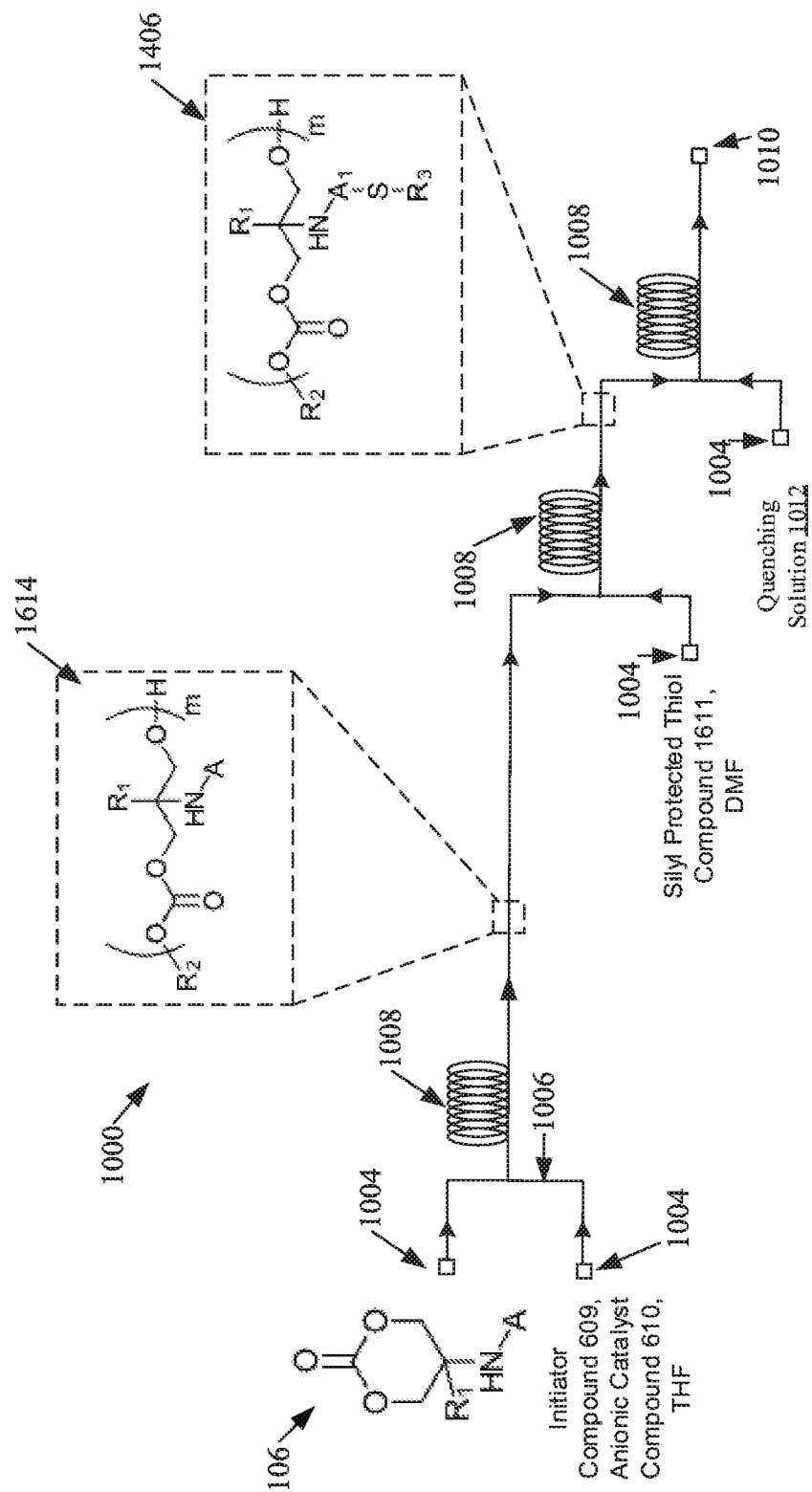
FIG. 20 illustrates a diagram of an example, non-limiting polymerization scheme that can be employed within a flow reactor system to polymerize and/or modify one or more polycarbonate polymers in accordance with one or more embodiments described herein.

FIG. 20 illustrates a diagram of the example, non-limiting polymerization scheme 1606 employed via flow reactor system 1000 in accordance with one or more embodiments described herein. Repetitive description of like elements employed in other embodiments described herein is omitted for sake of brevity. For example, the flow reactor system 1000 can facilitate the polymerization scheme 1606 and/or the various features of method 1500.

In accordance with example polymerization scheme 1606, the one or more functionalized cyclic carbonate monomers characterized by third cyclic carbonate chemical structure 106 can enter the one or more flow reactor system 1000 via one or more first inlets 1004, while the one or more initiator compounds 1609 and/or anionic catalyst compounds 1610 (e.g., in a solution with a solvent such as THF) can enter the one or more flow reactor system 1000 via one or more second inlets 1004. For example, the one or more initiator compounds 1609 and/or anionic catalyst compounds 1610 can be in accordance with the various features described herein with regards to method 1500. The one or more functionalized cyclic carbonate monomers characterized by third cyclic carbonate chemical structure 106 can meet and/or mix with the one or more initiator compounds 1609 and/or anionic catalyst compounds 1610 within the one or more channels 1006; thereby forming a stream of chemical reactants. As the stream flows through the one or more channels 1006, a polycarbonate platform characterized by the third polycarbonate platform chemical structure 1614 can be formed (e.g., as delineated by the dashed lines shown in FIG. 20).

Additionally, the polycarbonate platform characterized by third polycarbonate platform chemical structure 1614 can flow downstream through the one or more channels 1006 and mix with the one or more silyl protected thiol compounds 161 1and/or solvents (e.g., DMF) to facilitate a reaction that forms a functionalized polycarbonate polymer characterized by third polycarbonate chemical structure 1406. For example, the one or more silyl protected thiol compounds 1611 can enter the flow reactor system 1000 via one or more third inlets 1004 (e.g., in a solution with a solvent, such as DMF). In various embodiments, the introduction of the silyl protected thiol compound 1611 and/or the solvents can quench the polymerization reaction and catalyze the subsequent post polymerization modification reaction in flow. Further, the post polymerization modification reaction can be a nucleophilic aromatic substitution reaction, and can be facilitated by an additional set of reactor loops 1008. As the stream flows through the one or more channels 1006 and/or the second set of reactor loops 1008, the functionalized polycarbonate polymer characterized by the third polycarbonate chemical structure 1406 can be formed (e.g., as delineated by the dashed lines shown in FIG. 20). In one or more embodiments, the quenching solution 1012 (e.g., hydrochloric acid) can be further introduced into the flow reactor system 1000 via a fourth inlet 1004 to quench the post polymerization modification reaction. In one or more embodiments, the one or more ROPs and/or modification reactions can b e performed within the flow reactor system 1000 with a residence time that is greater than or equal to 1 and less than or equal to 1800 s.

While FIG. 20 depicts both the ROP reaction and the post polymerization modification reaction (e.g., nucleophilic aromatic substitution occurring in flow), the architecture of polymerization scheme 1606 is not so limited. For example, in one or more embodiments, the one or more ROPs can be performed in the flow reactor system 1000 (e.g., as shown in FIG. 20), and the resulting polycarbonate platforms characterized by third polycarbonate platform chemical structure 1614 can exit the flow reactor system 1000 and be employed in a batch reaction. For instance, the post polymerization nucleophilic aromatic substitution with the silyl protected thiol compound 1611 can be employed via a batch reaction process using one or more catalysts (e.g., DBU, DBU.OBz, BzOK, and/or BzONa).

Figure 21:
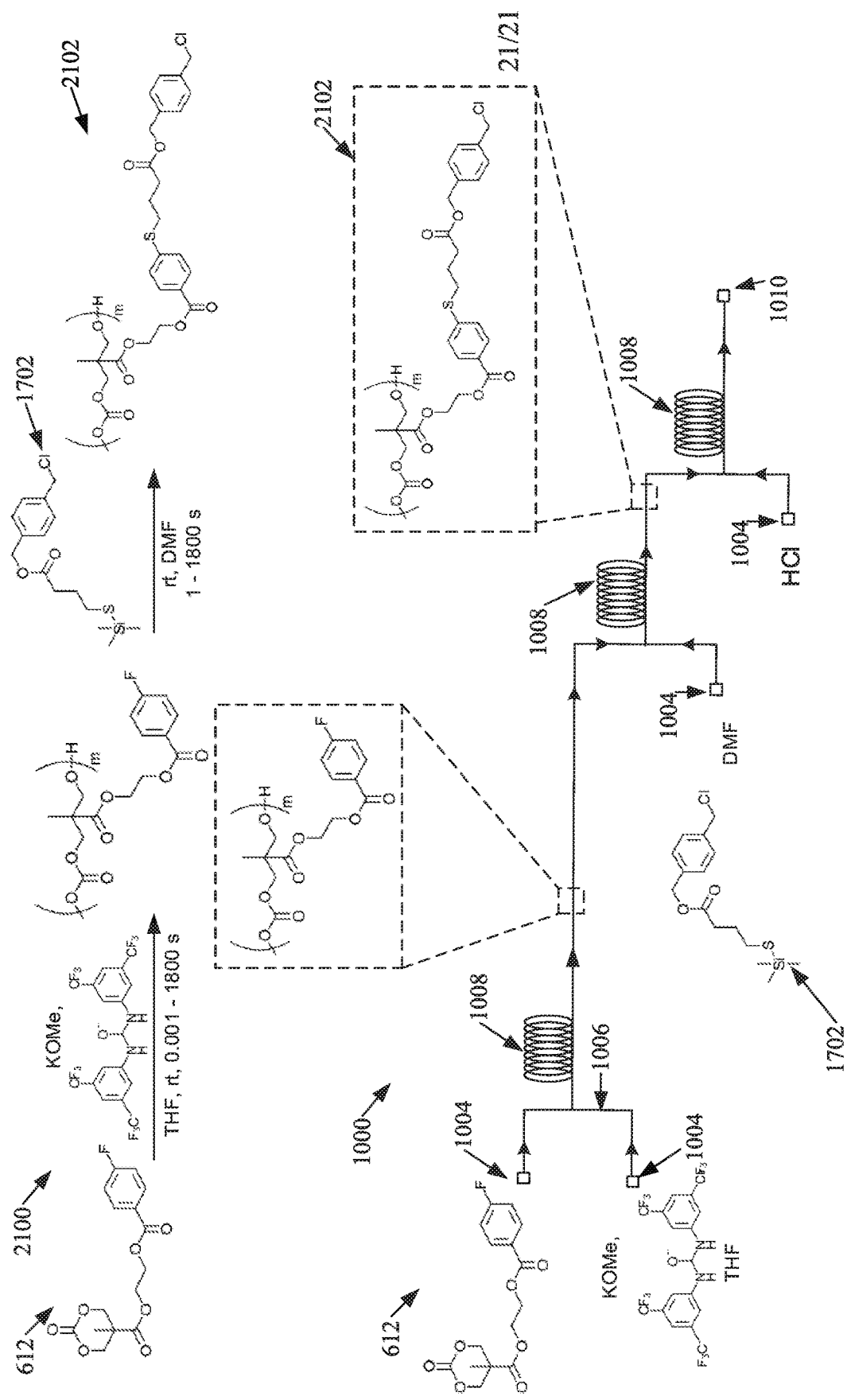
FIG. 21 illustrates a diagram of an example, non-limiting flow reactor system that can facilitate one or more polymerization schemes that can include post-polymerization modifications to one or more polycarbonate polymers in flow in accordance with one or more embodiments described herein.

FIG. 21 illustrates a diagram of a non-limiting example polymerization scheme 2100 that can be performed in accordance with the features of polymerizations scheme 1602 and/or facilitated by the flow reactor system 1000 in accordance with one or more embodiments described herein. Repetitive description of like elements employed in other embodiments described herein is omitted for sake of brevity. For example, the flow reactor system 1000 can facilitate the polymerization scheme 2100 and/or the various features of method 1500. FIG. 21 depicts the flow reactor system 1000 employed to facilitate an exemplary polymerization scheme 2100 in accordance with polymerization scheme 1602 to achieve functionalized polycarbonate polymer 2102 (e.g., characterized by the first polycarbonate chemical structure 1402). The exemplary polymerization scheme 2100 can comprise the ROP of the functionalized cyclic carbonate monomer 612 and a post polymerization modification with example chemical compound 1702 (e.g., an example silyl protected thiol compound 1611) to achieve the example functionalized polycarbonate polymer 2102.

In accordance with example polymerization scheme 2100, the one or more functionalized cyclic carbonate monomers 612 (e.g., characterized by first cyclic carbonate chemical structure 102) can enter the one or more flow reactor system 1000 via one or more first inlets 1004, while potassium methoxide "KOMe" (e.g., an example initiator compound 1609) and/or an anionic urea catalyst (e.g., an example anionic catalyst compound 610) in a solution with the solvent THF can enter the one or more flow reactor system 1000 via one or more second inlets 1004. The one or more functionalized cyclic carbonate monomers 612 can meet and/or mix with the one or more initiator compounds 609 (e.g., KOMe) and/or anionic catalyst compound 610 (e.g., a anionic urea compound, as shown in FIG. 21) within the one or more channels 1006; thereby forming a stream of chemical reactants. As the stream flows through the one or more channels 1006, a polycarbonate platform characterized by the polycarbonate platform chemical structure 1608 can be formed (e.g., as delineated by the dashed lines shown in FIG. 21).

Additionally, the polycarbonate platform can flow downstream through the one or more channels 1006 and mix with the silyl protected thiol compound 1611 (e.g., example chemical compound 1702 to facilitate a nucleophilic aromatic substitution reaction that forms the functionalized polycarbonate polymer 2102. For example, the silyl protected thiol compound 1611 (e.g., example chemical compound 1702) and/or the solvent (e.g., DMF) can enter the flow reactor system 1000 via one or more third inlets 1004. In various embodiments, the introduction of the silyl protected thiol compound 1611 (e.g., example chemical compound 1702) and/or the solvent (e.g., DMF) can quench the polymerization reaction and catalyze the subsequent post polymerization modification reaction in flow. Further, an additional set of reactor loops 1008 can facilitate the post polymerization reaction. As the stream flows through the one or more channels 1006 and/or the second set of reactor loops 1008, the functionalized polycarbonate polymer 2102 (e.g., as delineated by the dashed lines shown in FIG. 21). In one or more embodiments, the quenching solution 1012 (e.g., hydrochloric acid) can be further introduced into the flow reactor system 1000 via a fourth inlet 1004 to quench the post polymerization modification reaction.

While FIG. 21 depicts both the ROP reaction and the post polymerization modification reaction (e.g., nucleophilic aromatic substitution occurring in flow), the architecture of polymerization scheme 2100 is not so limited. For example, in one or more embodiments, the one or more ROPs can be performed in the flow reactor system 1000 (e.g., as shown in FIG. 21), and the resulting polycarbonate platforms characterized by polycarbonate platform chemical structure 1608 can exit the flow reactor system 1000 and be employed in a batch reaction. For instance, the post polymerization nucleophilic aromatic substitution with the example silyl protected thiol compound 1611 (e.g., example chemical compound 1702) can be employed via a batch reaction process using one or more catalysts (e.g., DBU, DBU.OBz, BzOK, and/or BzONa).

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form. As used herein, the terms "example" and/or "exemplary" are utilized to mean serving as an example, instance, or illustration. For the avoidance of doubt, the subject matter disclosed herein is not limited by such examples. In addition, any aspect or design described herein as an "example" and/or "exemplary" is not necessarily to be construed as preferred or advantageous over other aspects or designs, nor is it meant to preclude equivalent exemplary structures and techniques known to those of ordinary skill in the art.

It is, of course, not possible to describe every conceivable combination of components, products and/or methods for purposes of describing this disclosure, but one of ordinary skill in the art can recognize that many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim. The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A monomer, comprising:
   a cyclic carbonate molecular backbone covalently bonded to an aryl halide functional group in accordance with a chemical structure selected from a first group consisting of:

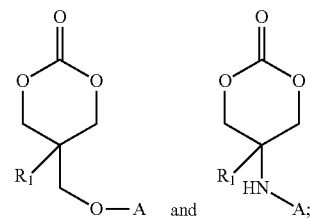

wherein $R_1$ is selected from a second group consisting of a hydrogen atom and a first alkyl group;

wherein A is the aryl halide functional group, and has a structure selected from a third group consisting of:

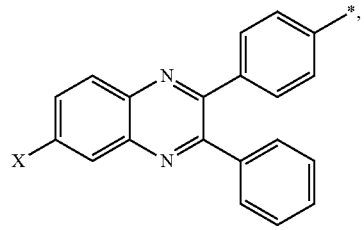

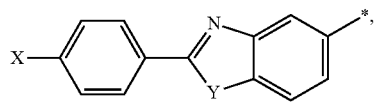

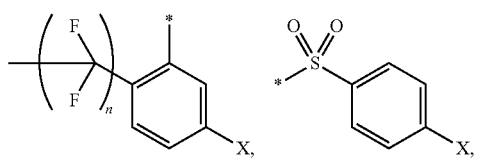

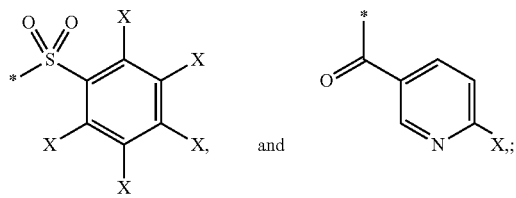

wherein X is a halide atom;

wherein Y is an atom selected from a fourth group consisting of an oxygen atom, a nitrogen atom, and a sulfur atom; and wherein n is an integer greater than or equal to 2 and less than or equal to 8.

2. The monomer of claim 1, wherein the first alkyl group comprises greater than or equal to one carbon atom and less than or equal to three carbon atoms.

3. The monomer of claim 1, wherein
X is the halide atom of fluorine.

4. The monomer of claim 1, wherein the cyclic carbonate molecular backbone is covalently bonded to the aryl halide functional group in accordance with chemical structure:

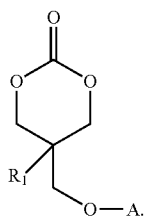

5. The monomer of claim 1, wherein the cyclic carbonate molecular backbone is covalently bonded to the aryl halide functional group in accordance with chemical structure:

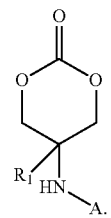

6. A monomer, comprising:

a cyclic carbonate molecular backbone covalently bonded to an aryl halide functional group in accordance with chemical structure:

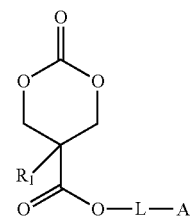

wherein $R_1$ is selected from a first group consisting of a hydrogen atom and a first alkyl group;

wherein L is an alkylene group with an end group selected from O or NH, wherein the end group is linked to A; and wherein A is the aryl halide functional group, and has a structure selected from a second group consisting of:

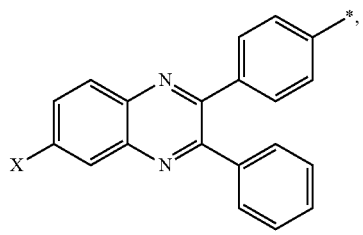

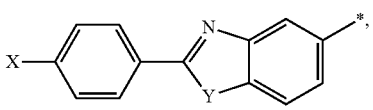

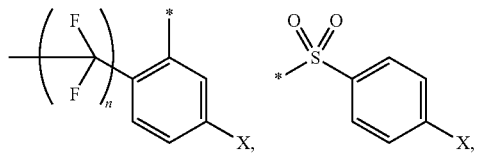

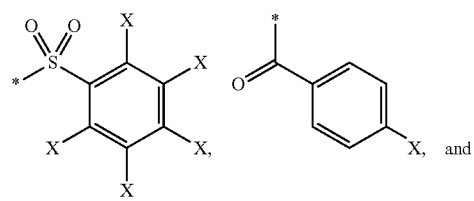

-continued

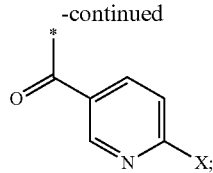

wherein X is a halide atom;
wherein Y is an atom selected from a third group consisting of an oxygen atom, a nitrogen atom, and a sulfur atom; and
wherein n is an integer greater than or equal to 2 and less than or equal to 8.

7. The monomer of claim 6, wherein the first alkyl group comprises greater than or equal to one carbon atom and less than or equal to three carbon atoms, and wherein the alkylene group comprises greater than or equal to one carbon atom and less than or equal to twenty carbon atoms.

8. The monomer of claim 6, wherein X is the halide atom of fluorine.

9. The monomer of claim 6, wherein X is the halide atom of chlorine.

10. The monomer of claim 6, wherein X is the halide atom of bromine.

11. The monomer of claim 6, wherein X is the halide atom of iodine.

12. The monomer of claim 6, with the chemical structure comprising:

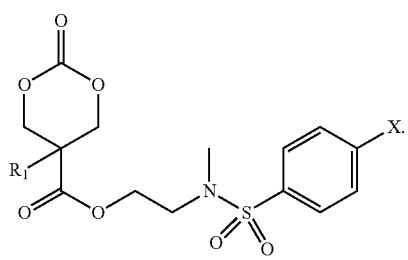

13. The monomer of claim 6, with the chemical structure comprising:

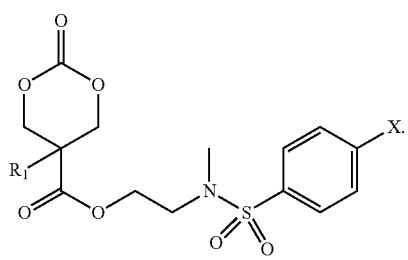

14. The monomer of claim 6, with the chemical structure comprising:

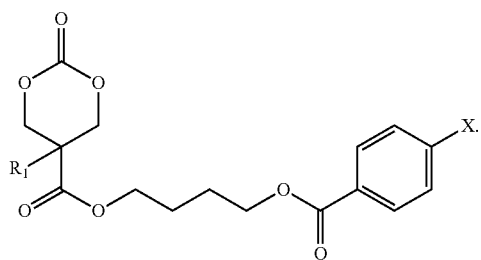

15. The monomer of claim 6, with the chemical structure comprising:

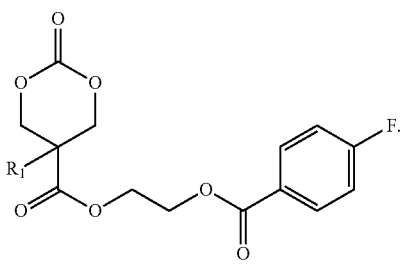

16. The monomer of claim 6, with the chemical structure comprising:

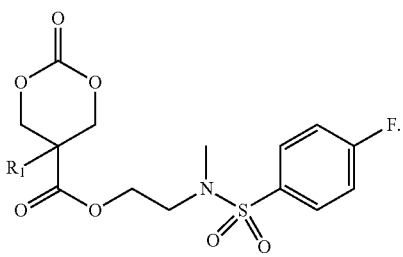

17. The monomer of claim 6, with the chemical structure comprising:

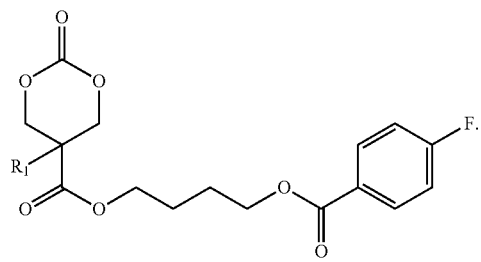

18. The monomer of claim 1, wherein X is the halide atom of chlorine.

19. The monomer of claim 1, wherein X is the halide atom of bromine.

20. The monomer of claim 1, wherein X is the halide atom of iodine.

* * * * *